(12) United States Patent
Wu et al.

(10) Patent No.: US 8,629,155 B2
(45) Date of Patent: Jan. 14, 2014

(54) ASPARTYL PROTEASE INHIBITORS

(75) Inventors: Yusheng Wu, New York, NY (US);
Ulrich Iserloh, Hoboken, NJ (US);
Jared N. Cumming, Garwood, NJ (US);
Xiaoxiang Liu, River vale, NJ (US);
Robert D. Mazzola, Stewartsville, NJ (US); Zhong-Yue Sun, Parlin, NJ (US);
Ying Huang, East Brunswick, NJ (US);
Andrew Stamford, Chatham, NJ (US);
Brian McKittrick, New Vernon, NJ (US); Zhaoning Zhu, Plainsboro, NJ (US)

(73) Assignee: Merck Sharp & Dohme, Corp., Rahway, NJ (US)

( * ) Notice: Subject to any disclaimer, the term of this patent is extended or adjusted under 35 U.S.C. 154(b) by 0 days.

(21) Appl. No.: 13/421,396

(22) Filed: Mar. 15, 2012

(65) Prior Publication Data

US 2012/0232064 A1 Sep. 13, 2012

Related U.S. Application Data

(63) Continuation of application No. 11/759,336, filed on Jun. 7, 2007, now Pat. No. 8,168,641.

(60) Provisional application No. 60/812,744, filed on Jun. 12, 2006.

(51) Int. Cl.
| | |
|---|---|
| *C07D 239/70* | (2006.01) |
| *C07D 513/20* | (2006.01) |
| *A01N 43/54* | (2006.01) |
| *A61P 31/18* | (2006.01) |
| *A61P 25/28* | (2006.01) |
| *A61P 9/00* | (2006.01) |

(52) U.S. Cl.
USPC .......................... 514/267; 544/249; 544/250

(58) Field of Classification Search
USPC .......................................... 544/250; 514/267
See application file for complete search history.

(56) References Cited

U.S. PATENT DOCUMENTS

| | | | |
|---|---|---|---|
| 2006/0110405 A1 * | 5/2006 | Buckheit .................. | 424/204.1 |
| 2007/0004730 A1 | 1/2007 | Zhou et al. | |
| 2007/0004786 A1 | 1/2007 | Malamas et al. | |
| 2007/0027199 A1 | 2/2007 | Malamas et al. | |
| 2007/0072925 A1 | 3/2007 | Malamas et al. | |
| 2007/0099875 A1 | 5/2007 | Zhu et al. | |
| 2007/0203116 A1 | 8/2007 | Quagliato et al. | |
| 2007/0232642 A1 | 10/2007 | Baxter et al. | |
| 2007/0259898 A1 | 11/2007 | Baxter et al. | |
| 2007/0287692 A1 | 12/2007 | Wu et al. | |
| 2008/0051420 A1 | 2/2008 | Berg et al. | |
| 2008/0058349 A1 | 3/2008 | Berg et al. | |
| 2008/0161269 A1 | 7/2008 | Berg et al. | |
| 2008/0214577 A1 | 9/2008 | Berg et al. | |
| 2008/0287460 A1 | 11/2008 | Burrows et al. | |
| 2008/0287462 A1 | 11/2008 | Chessari et al. | |
| 2009/0023762 A1 | 1/2009 | Berg et al. | |
| 2009/0062282 A1 | 3/2009 | Albert et al. | |
| 2009/0209529 A1 | 8/2009 | Andreini et al. | |

FOREIGN PATENT DOCUMENTS

| | | |
|---|---|---|
| WO | WO01/07440 | 2/2001 |
| WO | WO02/12243 | 2/2002 |
| WO | WO2003/035613 | 5/2003 |
| WO | WO 2008103351 | * 12/2004 |
| WO | WO2005/014540 | 2/2005 |
| WO | WO2005/016876 | 2/2005 |
| WO | WO2005108391 | 11/2005 |
| WO | WO2006/014762 | 2/2006 |
| WO | WO2006/014944 | 2/2006 |
| WO | WO 2006/017836 A2 | 2/2006 |
| WO | WO 2006/017844 A1 | 2/2006 |
| WO | WO 2006/024932 A1 | 3/2006 |
| WO | WO 2006/076284 A2 | 7/2006 |
| WO | WO2006/138192 | 12/2006 |
| WO | WO2006/138195 | 12/2006 |
| WO | WO2006/138217 | 12/2006 |

(Continued)

OTHER PUBLICATIONS

Maibaum, et al., Expert Opinion on Therapeutic Patents, "Renin inhibitors as Novel Treatments for Cardiovascular Disease," 2003, 589-603.*
Reuters, downloaded Jan. 2, 2013, http://www.huffingtonpost.com/2012/12/03/mk-8931-alzheimers-drug-trial-merck_n_2231306.html.*
Baxter, Ellen, et. al.; Journal of Medicinal Chemistry; vol. 50, No. 18, Sep. 6, 2007; "2-Amino-3,4-dihydroquinazolines as Inhibitors of BACE-1 . . . "; Published on Web on Aug. 8, 2007.

(Continued)

*Primary Examiner* — James O Wilson
*Assistant Examiner* — Cecilia M Jaisle
(74) *Attorney, Agent, or Firm* — Keith D. MacMillan; John C. Todaro

(57) ABSTRACT

Disclosed are compounds of formula I

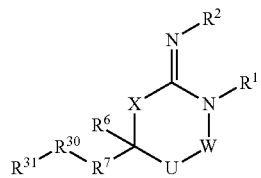

or a stereoisomer, tautomer, or pharmaceutically acceptable salt or solvate thereof, U, W, X, $R^1$, $R^2$, $R^6$, $R^7$, $R^{30}$ and $R^{31}$ are as described above in the specification.
Also disclosed is the method of inhibiting aspartyl protease, and in particular, the methods of treating cardiovascular diseases, cognitive and neurodegenerative diseases. Also disclosed are methods of treating cognitive or neurodegenerative diseases using the compounds of formula I in combination with a cholinesterase inhibitor or a muscarinic $m_1$ agonist or $m_2$ antagonist.

6 Claims, No Drawings

(56) References Cited

FOREIGN PATENT DOCUMENTS

| | | |
|---|---|---|
| WO | WO2006/138230 | 12/2006 |
| WO | WO2006/138264 | 12/2006 |
| WO | WO2006/138265 | 12/2006 |
| WO | WO2006/138266 | 12/2006 |
| WO | WO 2007/049532 A1 | 5/2007 |
| WO | WO 2007/050612 A1 | 5/2007 |
| WO | WO2007/050721 | 5/2007 |
| WO | WO2007/053506 | 5/2007 |
| WO | WO 2007/092839 A2 | 8/2007 |
| WO | WO 2007/092846 A2 | 8/2007 |
| WO | WO 2007/092854 A2 | 8/2007 |
| WO | WO2007/114771 A | 10/2007 |
| WO | WO 2007/114771 A1 | 10/2007 |
| WO | WO2007/146225 | 12/2007 |
| WO | WO 2007/149033 A1 | 12/2007 |
| WO | WO 2008/022024 A2 | 2/2008 |
| WO | WO2008/073365 | 6/2008 |
| WO | WO2008/073370 | 6/2008 |
| WO | WO2008/103351 | 8/2008 |
| WO | WO 2008/103351 A2 | 8/2008 |
| WO | WO 2008/133273 A1 | 11/2008 |
| WO | WO 2008/133274 A1 | 11/2008 |
| WO | WO 2009/005470 A1 | 1/2009 |
| WO | WO 2009/005471 A1 | 1/2009 |
| WO | WO 2009/022961 A1 | 2/2009 |
| WO | WO 2009/007300 A2 | 7/2009 |
| WO | WO 2009/091016 A1 | 7/2009 |
| WO | WO 2009/092566 A1 | 7/2009 |
| WO | WO 2009/097278 A1 | 8/2009 |
| WO | WO 2009/097401 A1 | 8/2009 |
| WO | WO 2009/108550 A1 | 9/2009 |
| WO | WO 2009/131974 A1 | 10/2009 |
| WO | WO 2009/131975 A1 | 10/2009 |
| WO | WO 2009/134617 A1 | 11/2009 |
| WO | WO 2009/151098 A1 | 12/2009 |
| WO | WO 2010/013302 A1 | 2/2010 |
| WO | WO 2010/013794 A1 | 2/2010 |
| WO | WO 2010/038686 A1 | 4/2010 |
| WO | WO 2010/047372 A1 | 4/2010 |
| WO | WO 2010/056194 A1 | 5/2010 |
| WO | WO 2010/059953 A1 | 5/2010 |

OTHER PUBLICATIONS

Buteau, Kristen C.; "Deuterated Drugs: Unexpectedly Nonobvious?", 10 J. High Tech L. 22 (2009).
Zhu, Zhaoning, et. al.; Journal of Medicinal Chemistry, vol. 53, No. 3, "Discovery of Cyclic Acylguanidines as Highly Potent and Selective . . . "; Sep. 21, 2009, pp. 951-965.
Nowak, Paweit, et. al.; Biiorganic and Medicinal Chemistry Letters; 20 (2010); "Discovery and initial optimization of 5, 5'-disubstituted aminohydantoins as potent . . . "; pp. 632-635.
Zhou, Ping, et. al.; Biiorganic and Medicinal Chemistry Letters; 20 (2010);"Pyridinyl aminohydantoins as small molecule BACE1 inhibitors"; pp. 2326-2329.
Malamas, Michael S.; et. al.; Biiorganic and Medicinal Chemistry Letters; 18 (2010); "Di-substituted pyridinyl aminohydantoins as potent and highly selective human . . . "; pp. 630-639.
Zhou, Ping; et. al.; "Pyridinylaminohydantoins as small molecule BACE-1 Inhibitors: Explorations of the S3 pocket", AN 2007:883652; 234TH ACS Conference Meeting Abstract; 2010 ACS on SciFinder.
Baxter, Ellen, et. al.; "BACE (Beta-Amyloid site Cleaving Enzyme, β-Secretase) Inhibitors for the treatment of Alzheimer's disease"; AN 2007:883605; 234TH ACS Conference Meeting Abstract; 2010 ACS on SciFinder.
Yan, Yinfa; et. al.; Piperidinyl-2-aminohydantoin derivatives for the inhibition of beta-secretase; AN 2007:295742; 233rd ACS National Meeting Abstract; 2010 ACS on SciFinder.
Erdel, Jim; et. al.; "Carbocylic substituted aminohydatoins as BACE-1 Inhibitors"; AN 2007:295741; 233rd ACS National Meeting Abstract; 2010 ACS on SciFinder.

Nowak, Pawei; et. al.; "Hit-to-lead optimization of aminohydantoins as b-Secretase Inhibitors"; AN 2007:295740; 233rd ACS National Meeting Abstract; 2010 ACS on SciFinder.
Malamas, Michael S.; et. al.; "Aminohydantoins as highly potent, selective and orally active BACE 1 Inhibitors", AN 2007-295667; 233RD Conference Meeting Abstract; 2010 ACS on SciFinder.
Malamas, Michael S.; et. al.; "Thienyl aminohydantoins as potent BACE1 Inhibitors", AN 2008:953770; 236th Conference Meeting Abstract; 2010 ACS on SciFinder.
Malamas, Michael S.; et. al.; "Pyrazinyl aminohydantoins as potent BACE1 Inhibitors", AN 2008:953771; 236th Conference Meeting Abstract; 2010 ACS on SciFinder.
Malamas, Michael S.; et. al.;"Pyrrolyl 2-aminopyridines as potent BACE1 Inhibitors", 238th Conference Meeting Abstract; 2010 ACS on SciFinder.
Zhou, Ping; et. al.; "Substituted-pyrrole 2-amino-3,5-dihydro-4H-imidazol-4-ones as highly potent BACE1 Inhibitors: Optimization of the S3 pocket"; 235th Conference Meeting Abstract; 2010 ACS on SciFinder.
Yan, Yinfa; et. al.; "Syntheses and biological properties of carbocylic substituted aminohydantoin derivatives", AN 2008:389811; 235th Conference Meeting Abstract; 2010 ACS on SciFinder.
Quagliato, Dominick; et. al.; "Rigid analogs of 4,4-diaryl-iminohydantoins as potent inhibitors of Beta-secretase", AN 2008:389810; 235th Conference Meeting Abstract; 2010 ACS on SciFinder.
Solvibile, William R.; et. al.; "2-Substituted-pyrrole 2-amino-3,5-dihydro-4H-imidazol-4-ones: Highly potent and selective BACE1 Inhibitors", AN 2008:389809; 235th Conference Meeting Abstract; 2010 ACS on SciFinder.
Erdel, Jim; et. al.; "N-Alkyl substituted-pyrrole 2-amino-3,5-dihydro-4H-imidazol-4-ones as potent, and selective BACE 1 Inhibitors", AN 2008:389808; 235th Conference Meeting Abstract; 2010 ACS on SciFinder.
Fobare, William F. et. al.; "Substituted-pyrrole 2-amino-3,5-dihydro-4h-imidazol-4-ones as highly potent and selective BACE1 Inhibitors", AN 2008:389736; 235th Conference Meeting Abstract; 2010 ACS on SciFinder.
Fan, Kristi Yi; et. al.; "Structure-based lead optimization of small molecule β-secretase(BACE1) Inhibitors", AN 2008:387238; 235th Conference Meeting Abstract; 2010 ACS on SciFinder.
Zhu, Zhaoning, et. al.; "Discovery of cyclic-aclguanidines as potent and selective BACE1 Inhibitors", AN 2009: 984464; 238th Conference Meeting Abstract; 2010 ACS on SciFinder.
Cuming, Jared, et. al.; Optimization of the iminohydantoin series of BACE1 Inhibitors. Part 4: Explorations of the F' subsite in the C5-aryl series; AN 2009:984451; 2010 ACS on SciFinder.
Smith, Elizabeth, et. al.; "Optimization of the iminohydantoin series of BACE1 Inhibitors. Part 5: Exploration of the S1' and S2-S3 binding sites"; AN 2009:984450; 238th Conference Meeting Abstract; 2010 ACS on SciFinder.
Mazzola, Robert, D.; et. al.; "Design and synthesis of novel iminohydatoin β-secretase (BACE) Inhibitors. Part 3: Discovery and Exploration of the A-site"; AN 2009:984449; 238th Conference Meeting Abstract; 2010 ACS on SciFinder.
Mazzola, Robert, D.; et. al.;"Novel iminopyrimidinone β-secretase (BACE)Inhibitors: Part 3: C5 Substititution"; AN 2010:345058; 239th Conference Meeting Abstract; 2010 ACS on SciFinder.
Caldwell, John, et. al.; Design and synthesis of novel iminohydatoin β-secretase (BACE) Inhibitors. Part 2: The S1 to S3 approach; AN 2009:984447; 238th Conference Meeting Abstract; 2010 ACS on SciFinder.
Sun Zhong-Yue, et. al.; "2- iminohydatoin as potential BACE1 Inhibitors"; AN 2009:984446; 238th Conference Meeting Abstract; 2010 ACS on SciFinder.
Efremov, Ivan V., et. al.; "Identificaiton of spirocycli pyrrolidines as novel BACE Inhibitors"; AN2010:345057; 239th Conference Meeting Abstract; 2010 ACS on SciFinder.
Iserloh, Ulrich; et. al.; Novel iminopyrimidinone β-secretase (BACE)Inhibitors: Part 2. P1-azoles AN 2010:345056; 239th Conference Meeting Abstract; 2010 ACS on SciFinder.

(56) References Cited

OTHER PUBLICATIONS

Robichaud, Albert J.; et. al.; Identification of selective BACE1 inhibitors as potential disease modifying treatments for Alzheimer's disease: AN 2010:344829; 239th Conference Meeting Abstract; 2010 ACS on SciFinder.

Brodney, Michael A.; et. al.; "Beta-secretase inhibitors for the treatment of Alzheimer's disease", AN2010:344828; 239th Conference Meeting Abstract; 2010 ACS on SciFinder.

Stamford, Andrew.W.; et. al.; "Discovery of small molecule, orally active and brain penetrant BACE 1 Inhibitors", AN 2010: 344827; 239th Conference Meeting Abstract; 2010 ACS on SciFinder.

O'Neill, Brian T.; et. al.; "Pyrrolidine ss-secretase inhibitors for the treatment of Alzheimer's disease", AN 2010: 344728; 239th Conference Meeting Abstract; 2010 ACS on SciFinder.

Cumming, Jared N.; Novel iminopyrimidinone β-secretase (BACE)Inhibitors: Part 1, P1-P3 SAR; AN 2010:344544; 239th Conference Meeting Abstract; 2010 ACS on SciFinder.

Barton, H.J., et al., "On the Structure of some Substituted 4,6-Pyrimidinediones", Polish J. Chem., 1995, pp. 235-245, vol. 69.

Garratt, Peter J., et al., "A Novel Synthesis of Dihydropyrimidines", J. Chem. Soc., Chem. Commun., 1987, pp. 568-569.

Kwon, Chul-Hoon, et al., "Facile Synthesis of Substituted 2-Iminohydantoins", Synthetic Communications, 1987, pp. 1677-1682, vol. 17, No. 14.

Lin, Peishan, et al., "Synthesis of Novel Guanidinoglycoside: 2-Glycosylamino 4,5-dihydro-6-pyrimidinone", J. Org. Chem., 2001, pp. 8243-8247, vol. 66, No. 24.

Talaty, Erach R., et al., "Preparation of Substituted Imidazolidinones and Hydantoins by Ring-Expansion of Aziridinones", Synlett, 1997, pp. 683-684. vol. 6.

Weber, W. et al., "First synthesis of the main metabolite of secobarbital", Pharmazie, 1998, pp. 771-775, vol. 53, No. 11.

Yusoff, Mashitah M., et al., "Ring-Expansion of an Aziridinone to a Hexahydrotriazine through the Agency of a Novel Rearrangement", Tetrahedron Letters, 1996, pp. 8695-8698, vol. 37, No. 48.

International Search Report for PCT/US2007/013684, mailed Jan. 25, 2008 (4 pages).

U.S. Appl. No. 11/759,336, filed Jun. 7, 2007.

Abstract: Albert, Jeffrey S.; et. al.; "Fragment based lead generation approaches for inhibitors of beta-secretase: Development of a novel series of isocytosine-based inhibitors"; (2007) AN 2007:295744.

ROC (Taiwan) Patent Application No. 093138776 Search Report, Sep. 2007—1 page Translation.

* cited by examiner

ASPARTYL PROTEASE INHIBITORS

CROSS-REFERENCE TO RELATED APPLICATIONS

This application is a Continuation application of U.S. patent application Ser. No. 11/759,336, filed Jun. 7, 2006, pending, which claims priority to U.S. Provisional Application No. 60/812,744, filed Jun. 12, 2006, each of which is incorporated herein by reference.

FIELD OF THE INVENTION

This invention relates to aspartyl protease inhibitors, pharmaceutical compositions comprising said compounds, their use in the treatment of cardiovascular diseases, cognitive and neurodegenerative diseases, and their use as inhibitors of the Human Immunodeficiency Virus, plasmepsins, cathepsin D and protozoal enzymes.

BACKGROUND

There are a number of aspartic proteases known to date, including pepsin A and C, renin, BACE, BACE 2, Napsin A, and cathepsin D, which have been implicated in pathological conditions. The role of renin-angiotensin system (RAS) in regulation of blood pressure and fluid electrolyte has been well established (Oparil, S, et al. N Engl J Med 1974; 291: 381-401/446-57). The octapeptide Angiotensin-II, a potent vasoconstrictor and stimulator for release of adrenal aldosterone, was processed from the precursor decapeptide Angiotensin-I, which in turn is processed from angiotensinogen by the renin enzyme. Angiotensin-II is also found to play roles in vascular smooth muscle cell growth, inflammation, reactive oxygen species generation and thrombosis and influence atherogenesis and vascular damage. Clinically, the benefit of interruption of the generation of angiotensin-II through antagonism of conversion of angiotensin-I has been well known and there are a number of ACE inhibitor drugs on the market. The blockade of the earlier conversion of angiotensinogen to angiotensin-I, i.e. the inhibition of renin enzyme, is expected to have similar but not identical effects. Since renin is an aspartyl protease whose only natural substrate is angiotensinogen, it is believed that there would be less frequent adverse effect for controlling high blood pressure and related symptoms regulated by angiotensin-II through its inhibition.

Another protease, Cathepsin-D, is involved in lysosomal biogenesis and protein targeting, and may also be involved in antigen processing and presentation of peptide fragments. It has been linked to numerous diseases including, Alzheimer's, Disease, connective tissue disease, muscular dystrophy and breast cancer.

Alzheimer's Disease (AD) is a progressive neurodegenerative disease that is ultimately fatal. Disease progression is associated with gradual loss of cognitive function related to memory, reasoning, orientation and judgment. Behavioral changes including confusion, depression and aggression also manifest as the disease progresses. The cognitive and behavioral dysfunction is believed to result from altered neuronal function and neuronal loss in the hippocampus and cerebral cortex. The currently available AD treatments are palliative, and while they ameliorate the cognitive and behavioral disorders, they do not prevent disease progression. Therefore there is an unmet medical need for AD treatments that halt disease progression.

Pathological hallmarks of AD are the deposition of extracellular β-amyloid (Aβ) plaques and intracellular neurofibrillary tangles comprised of abnormally phosphorylated protein tau. Individuals with AD exhibit characteristic Aβ deposits, in brain regions known to be important for memory and cognition. It is believed that Aβ is the fundamental causative agent of neuronal cell loss and dysfunction which is associated with cognitive and behavioral decline. Amyloid plaques consist predominantly of Aβ peptides comprised of 40-42 amino acid residues, which are derived from processing of amyloid precursor protein (APP). APP is processed by multiple distinct protease activities. Aβ peptides result from the cleavage of APP by β-secretase at the position corresponding to the N-terminus of Aβ, and at the C-terminus by γ-secretase activity. APP is also cleaved by α-secretase activity resulting in the secreted, non-amyloidogenic fragment known as soluble APP.

An aspartyl protease known as BACE-1 has been identified as the β-secretase activity responsible for cleavage of APP at the position corresponding to the N-terminus of Aβ peptides.

Accumulated biochemical and genetic evidence supports a central role of Aβ in the etiology of AD. For example, Aβ has been shown to be toxic to neuronal cells in vitro and when injected into rodent brains. Furthermore inherited forms of early-onset AD are known in which well-defined mutations of APP or the presenilins are present. These mutations enhance the production of Aβ and are considered causative of AD.

Since Aβ peptides are formed as a result of β-secretase activity, inhibition of BACE-1 should inhibit formation of Aβ peptides. Thus inhibition of BACE-1 is a therapeutic approach to the treatment of AD and other cognitive and neurodegenerative diseases caused by Aβ plaque deposition.

Human immunodeficiency virus (HIV), is the causative agent of acquired immune deficiency syndrome (AIDS). It has been clinically demonstrated that compounds such as indinavir, ritonavir and saquinavir which are inhibitors of the HIV aspartyl protease result in lowering of viral load. As such, the compounds described herein would be expected to be useful for the treatment of AIDS. Traditionally, a major target for researchers has been HIV-1 protease, an aspartyl protease related to renin.

In addition, Human T-cell leukemia virus type I (HTLV-I) is a human retrovirus that has been clinically associated with adult T-cell leukemia and other chronic diseases. Like other retroviruses, HTLV-I requires an aspartyl protease to process viral precursor proteins, which produce mature virions. This makes the protease an attractive target for inhibitor design. (Moore, et al. Purification of HTLV-I Protease and Synthesis of Inhibitors for the treatment of HTLV-I Infection 55th Southeast Regional Meeting of the American Chemical Society, Atlanta, Ga., US Nov. 16-19, 2003 (2003), 1073. CODEN; 69EUCH Conference, AN 2004:137641 CAPLUS).

Plasmepsins are essential aspartyl protease enzymes of the malarial parasite. Compounds for the inhibition of aspartyl proteases plasmepsins, particularly I, II, IV and HAP, are in development for the treatment of malaria. (Freire, et al. WO 2002074719. Na Byoung-Kuk, et al., Aspartic proteases of *Plasmodium vivax* are highly conserved in wild isolates, Korean Journal of Parasitology (2004 June), 42(2) 61-6. Journal code: 9435800) Furthermore, compounds used to target aspartyl proteases plasmepsins (e.g. I, II, IV and HAP), have been used to kill malarial parasites, thus treating patients thus afflicted.

Compounds that act as aspartyl protease inhibitors are described, for example in application U.S. Ser. No. 11/010, 772, filed on Dec. 13, 2004, herein incorporated by reference.

WO/9304047, herein incorporated by reference, describes compounds having a quinazolin-2-(thi)one nucleus. The document alleges that the compounds described therein are inhibitors of HIV reverse transcriptase.

US Publication No. US 2005/0282826 A1, herein incorporated by reference, describes diphenylimidazopyrimidine or -imidazole amines, which are said to be useful for the therapeutic treatment, prevention or amelioration of a disease or disorder characterized by elevated β-amyloid deposits or β-amyloid levels in a patient. Disease states mentioned in the publication include Alzheimer's disease, mild cognitive impairment, Down's syndrome, hereditary cerebral hemorrhage with amyloidosis of the Dutch type, cerebral amyloid angiopathy and degenerative dementia.

US Publication No. US 2005/0282825 A1, herein incorporated by reference, describes amino-5,5-diphenylimidazolones, which are said to be useful for the therapeutic treatment, prevention or amelioration of a disease or disorder characterized by elevated β-amyloid deposits or β-amyloid levels in a patient. Disease states mentioned in the publication include Alzheimer's disease, mild cognitive impairment, Down's syndrome, hereditary cerebral hemorrhage with amyloidosis of the Dutch type, cerebral amyloid angiopathy and degenerative dementia.

Other publications that disclosed compounds that are useful for treating Alzherimer's disease include WO 2006/044492, which discloses spiropiperidine compounds that are said to be inhibitors of β-secretase, and WO 2006/041404, which discloses substituted amino compounds that are said to be useful for the treatment or prophylaxix of Aβ related pathologies. Both these publications are incorporated by reference.

SUMMARY OF THE INVENTION

The present invention relates to compounds having the structural formula I

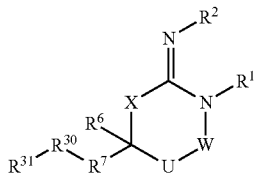

I or a stereoisomer, tautomer, or pharmaceutically acceptable salt or solvate thereof, wherein W is a bond, —C(=S)—, —S(O)—, —S(O)$_2$—, —C(=O)—, —O—, —C(R$^6$)(R$^7$)—, —N(R$^5$)— or —C(=N(R$^5$))—;

X is —O—, —N(R$^5$)— or —C(R$^6$)(R$^7$)—;

U is a bond or —(C(R$^3$)(R$^4$))$_b$—, wherein b is 1 or 2;

R$^1$, R$^2$ and R$^5$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —OR$^{15}$, —CN, —C(=NR$^{11}$)R$^8$, —C(O)R$^8$, —C(O)OR$^9$, —S(O)R$^{10}$, —S(O)$_2$R$^{10}$, —C(O)N(R$^{11}$)(R$^{12}$), —S(O)N(R$^{11}$)(R$^{12}$), —S(O)$_2$N(R$^{11}$)(R$^{12}$), —NO$_2$, —N=C(R$^8$)$_2$ and —N(R$^{11}$)(R$^{12}$), provided that R$^1$ and R$^5$ are not both selected from —NO$_2$, —N=C(R$^8$)$_2$ and —N(R$^{11}$)(R$^{12}$);

R$^3$, R$^4$ and R$^6$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CH$_2$—O—Si(R$^9$)(R$^{10}$)(R$^{19}$), —SH, —CN, —OR$^9$, —C(O)R$^8$, —C(O)OR$^9$, —C(O)N(R$^{11}$)(R$^{12}$), —SR$^{19}$, —S(O)N(R$^{11}$)(R$^{12}$), —S(O)$_2$N(R$^{11}$)(R$^{12}$), —N(R$^{11}$)(R$^{12}$), —N(R$^{11}$)C(O)R$^8$, —N(R$^{11}$)S(O)R$^{10}$, —N(R$^{11}$)S(O)$_2$R$^{10}$, —N(R$^{11}$)C(O)N(R$^{12}$)(R$^{13}$), —N(R$^{11}$)C(O)OR$^9$ and —C(=NOH)R$^8$;

R$^7$ is independently selected from the group consisting of alkylene, arylalkylene, heteroarylalkylene, cycloalkylalkylene, heterocycloalkylalkylene, arylcycloalkylalkylene, heteroarylcycloalkylalkylene, arylheterocycloalkylalkylene, heteroarylheterocycloalkylalkylene, cycloalkylene, arylcycloalkylene, heteroarylcycloalkylene, heterocycloalkylene, arylheterocycloalkylene, heteroarylheterocycloalkylene, alkenylene, arylalkenylene, cycloalkenylene, arylcycloalkenylene, heteroarylcycloalkenylene, heterocycloalkenylene, arylheterocycloalkenylene, heteroarylheterocycloalkenylene, alkynylene, arylalkynylene, arylene, cycloalkylarylene, heterocycloalkylarylene, cycloalkenylarylene, heterocycloalkenylarylene, heteroarylene, cycloalkylheteroarylene, heterocycloalkylheteroarylene, cycloalkenylheteroarylene and heterocycloalkenylheteroarylene, wherein each of said R$^7$ groups is independently unsubstituted or substituted at 1 to 3 hydrogens by 1 to 3 R$^{21}$ groups;

provided that when W is —O— or —N(R$^5$)—, then R$^3$ and R$^4$ are not halo, —SH, —OR$^9$, —SR$^{19}$, —S(O)N(R$^{11}$)(R$^{12}$), —S(O)$_2$N(R$^{11}$)(R$^{12}$), —N(R$^{11}$)(R$^{12}$), —N(R$^{11}$)C(O)R$^8$, —N(R$^{11}$)S(O)R$^{10}$, —N(R$^{11}$)C(O)N(R$^{12}$)(R$^{13}$), or —N(R$^{11}$)C(O)OR$^9$;

or R$^3$, R$^4$, R$^6$ and R$^7$, together with the carbon to which they are attached, form a 3-7 membered cycloalkyl group optionally substituted by R$^{14}$ or a 3-7 membered cycloalkylether optionally substituted by R$^{14}$;

or R$^3$ and R$^4$ together with the carbon to which they are attached, are combined to form multicyclic groups such as

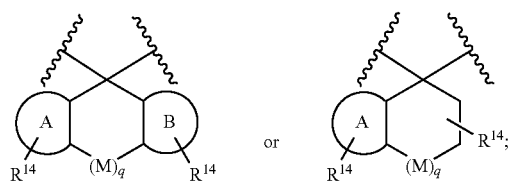

wherein M is —CH$_2$—, S, —N(R$^{19}$)— or O, A and B are independently arylene or heteroarylene and q is 0, 1 or 2 provided that when q is 2, one M must be a carbon atom and when q is 2, M is optionally a double bond; and with the proviso that when R$^3$ and R$^4$ form said multicyclic groups;

then adjacent $R^3$ and $R^4$ or $R^6$ and $R^7$ groups cannot be combined to form said multicyclic groups;

or $R^6$ and $R^7$ together with the carbon to which they are attached, are combined to form multicyclic groups such as

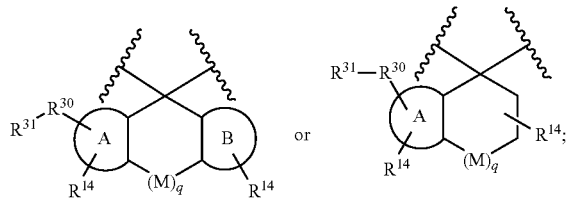

wherein M is —CH$_2$—, S, —N(R$^{19}$)— or O, A and B are independently arylene or heteroarylene and q is 0, 1 or 2 provided that when q is 2, one M must be a carbon atom and when q is 2, M is optionally a double bond; and with the proviso that when $R^6$ and $R^7$ form said multicyclic groups, then adjacent $R^3$ and $R^4$ or $R^6$ and $R^7$ cannot be combined to form said multicyclic groups;

$R^8$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —OR$^{15}$, —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$) and —N(R$^{15}$)C(O)OR$^{16}$;

$R^9$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, and heterocycloalkenylheteroaryl;

$R^{10}$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl and —N(R$^{15}$)(R$^{16}$);

$R^{11}$, $R^{12}$ and $R^{13}$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —C(O)R$^8$, —C(O)OR$^9$, —S(O)R$^{10}$, —S(O)$_2$R$^{10}$, —C(O)N(R$^{15}$)(R$^{16}$), —S(O)N(R$^{15}$)(R$^{16}$), —S(O)$_2$N(R$^{15}$)(R$^{16}$) and —CN;

$R^{14}$ is 1-5 substituents independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$) and —N(R$^{15}$)C(O)OR$^{16}$;

$R^{15}$, $R^{16}$ and $R^{17}$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, R$^{18}$-alkyl, R$^{18}$-arylalkyl, R$^{18}$-heteroarylalkyl, R$^{18}$-cycloalkylalkyl, R$^{18}$-heterocycloalkylalkyl, R$^{18}$-arylcycloalkylalkyl, R$^{18}$-heteroarylcycloalkylalkyl, R$^{18}$-arylheterocycloalkylalkyl, R$^{18}$-heteroarylheterocycloalkylalkyl, R$^{18}$-cycloalkyl, R$^{18}$-arylcycloalkyl, R$^{18}$-heteroarylcycloalkyl, R$^{18}$-heterocycloalkyl, R$^{18}$-arylheterocycloalkyl, R$^{18}$-heteroarylheterocycloalkyl, R$^{18}$-alkenyl, R$^{18}$-arylalkenyl, R$^{18}$-cycloalkenyl, R$^{18}$-arylcycloalkenyl, R$^{18}$-heteroarylcycloalkenyl, R$^{18}$-heterocycloalkenyl, R$^{18}$-arylheterocycloalkenyl, R$^{18}$-heteroarylheterocycloalkenyl, R$^{18}$-alkynyl, R$^{18}$-arylalkynyl, R$^{18}$-aryl, R$^{18}$-cycloalkylaryl, R$^{18}$-heterocycloalkylaryl, R$^{18}$-cycloalkenylaryl, R$^{18}$-heterocycloalkenylaryl, R$^{18}$-heteroaryl, R$^{18}$-cycloalkylheteroaryl, R$^{18}$-heterocycloalkylheteroaryl, R$^{18}$-cycloalkenylheteroaryl, and R$^{18}$-heterocycloalkenylheteroaryl; or $R^{15}$, $R^{16}$ and $R^{17}$ are

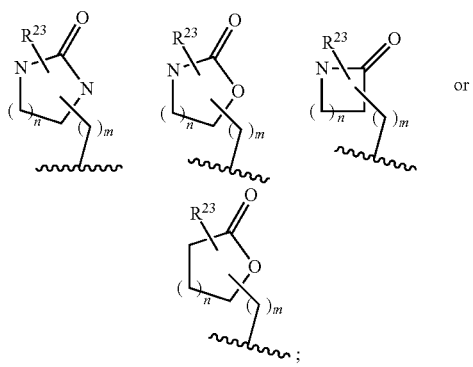

wherein $R^{23}$ numbers 0 to 5 substituents, m is 0 to 6 and n is 0 to 5;

$R^{18}$ is 1-5 substituents independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —$NO_2$, halo, HO-alkoxyalkyl, —$CF_3$, —CN, alkyl-CN, —C(O)$R^{19}$, —C(O)OH, —C(O)O$R^{19}$, —C(O)NH$R^{20}$, —C(O)$NH_2$, —C(O)$NH_2$—C(O)N(alkyl)$_2$, —C(O)N(alkyl)(aryl), —C(O)N(alkyl)(heteroaryl), —S$R^{19}$, —S(O)$_2R^{20}$, —S(O)$NH_2$, —S(O)NH(alkyl), —S(O)N(alkyl)(alkyl), —S(O)NH(aryl), —S(O)$_2NH_2$, —S(O)$_2$NH$R^{19}$, —S(O)$_2$NH (heterocycloalkyl), —S(O)$_2$N(alkyl)$_2$, —S(O)$_2$N(alkyl)(aryl), —OC$F_3$, —OH, —O$R^{20}$, —O-heterocycloalkyl, —O-cycloalkylalkyl, —O-heterocycloalkylalkyl, —$NH_2$, —NH$R^{20}$, —N(alkyl)$_2$, —N(arylalkyl)$_2$, —N(arylalkyl)- (heteroarylalkyl), —NHC(O)$R^{20}$, —NHC(O)$NH_2$, —NHC (O)NH(alkyl), —NHC(O)N(alkyl)(alkyl), —N(alkyl)C(O) NH(alkyl), —N(alkyl)C(O)N(alkyl)(alkyl), —NHS(O)$_2R^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or two $R^{18}$ moieties on adjacent carbons can be linked together to form

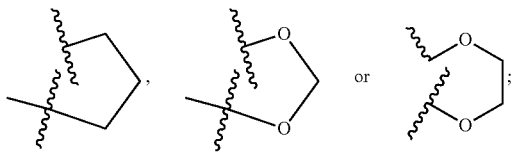

$R^{19}$ is alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl;

$R^{20}$ is halo substituted aryl, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl, and wherein each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl groups in $R^1$, $R^2$, $R^3$, $R^4$, $R^5$, $R^6$, $R^8$, $R^9$, $R^{10}$, $R^{11}$, $R^{12}$, $R^{13}$ and $R^{14}$ are independently unsubstituted or substituted by 1 to 5 $R^{21}$ groups independently selected from the group consisting alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CN, —C(=N$R^{11}$)$R^{15}$, —O$R^{15}$, —C(O)$R^{15}$, —C(O)O$R^{15}$, —C(O)N($R^{15}$)($R^{16}$), —S$R^{15}$, —S(O)N($R^{15}$)($R^{16}$), —CH($R^{15}$)($R^{16}$), —S(O)$_2$N($R^{15}$)($R^{16}$), —C(=NO$R^{15}$)$R^{16}$, —P(O)(O$R^{15}$)(O$R^{16}$), —N($R^{15}$)($R^{16}$), -alkyl-N($R^{15}$)($R^{16}$), —N($R^{15}$)C(O)$R^{16}$, —$CH_2$—N($R^{15}$)C(O)$R^{16}$, —$CH_2$—N ($R^{15}$)C(O)N($R^{16}$)($R^{17}$), —$CH_2$—$R^{15}$; —$CH_2$N($R^{15}$)($R^{16}$), —N($R^{15}$)S(O)$R^{16}$, —N($R^{15}$)S(O)$_2R^{16}$, —$CH_2$—N($R^{15}$)S (O)$_2R^{16}$, —N($R^{15}$)S(O)$_2$N($R^{16}$)($R^{17}$), —N($R^{15}$)S(O)N($R^{16}$) ($R^{17}$), —N($R^{15}$)C(O)N($R^{16}$)($R^{17}$), —$CH_2$—N($R^{15}$)C(O)N ($R^{16}$)($R^{17}$), —N($R^{15}$)C(O)O$R^{16}$, —$CH_2$—N($R^{15}$)C(O) O$R^{16}$, —S(O)$R^{15}$, —$N_3$, —$NO_2$ and —S(O)$_2R^{15}$;

and wherein each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl groups in $R^{21}$ are independently unsubstituted or substituted by 1 to 5 $R^{22}$ groups independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CN, —C(=NR$^{11}$)R$^{15}$, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —CH(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —CH$_2$—N(R$^{15}$)C(O)N(R$^{16}$)(R$^{17}$), —CH$_2$—R$^{15}$; —CH$_2$N(R$^{15}$)(R$^{16}$), —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —S(O)R$^{15}$, —N$_3$, —NO$_2$ and —S(O)$_2$R$^{15}$;

$R^{23}$ is 1 to 5 groups independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CN, —OR$^{24}$, —C(O)R$^{24}$, —C(O)OR$^{24}$, —C(O)N(R$^{24}$)(R$^{25}$), —SR$^{24}$, —S(O)N(R$^{24}$)(R$^{25}$), —S(O)$_2$N(R$^{24}$)(R$^{25}$), —C(=NOR$^{24}$)R$^{25}$, —P(O)(OR$^{24}$)(OR$^{25}$), —N(R$^{24}$)(R$^{25}$), -alkyl-N(R$^{24}$)(R$^{25}$), —N(R$^{24}$)C(O)R$^{25}$, —CH$_2$—N(R$^{24}$)C(O)R$^{25}$, —N(R$^{24}$)S(O)R$^{25}$, —N(R$^{24}$)S(O)$_2$R$^{25}$, —CH$_2$—N(R$^{24}$)S(O)$_2$R$^{25}$, —N(R$^{24}$)S(O)$_2$N(R$^{25}$)(R$^{26}$), —N(R$^{24}$)C(O)N(R$^{25}$)(R$^{26}$), —CH$_2$—N(R$^{24}$)C(O)N(R$^{25}$)(R$^{26}$), —N(R$^{24}$)C(O)OR$^{25}$, —CH$_2$—N(R$^{24}$)C(O)OR$^{25}$, —S(O)R$^{24}$ and —S(O)$_2$R$^{24}$; and wherein each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl and heterocycloalkenylheteroaryl groups in $R^{23}$ are independently unsubstituted or substituted by 1 to 5 $R^{27}$ groups independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalk-enyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CF$_3$, —CN, —OR$^{24}$, —C(O)R$^{24}$, —C(O)OR$^{24}$, alkyl-C(O)OR$^{24}$, —C(O)N(R$^{24}$)(R$^{25}$), —SR$^{24}$, —S(O)N(R$^{24}$)(R$^{25}$), —S(O)$_2$N(R$^{24}$)(R$^{25}$), —C(=NOR$^{24}$)R$^{25}$, —P(O)(OR$^{24}$)(OR$^{25}$), —N(R$^{24}$)(R$^{25}$), -alkyl-N(R$^{24}$)(R$^{25}$), —N(R$^{24}$)C(O)R$^{25}$, —CH$_2$—N(R$^{24}$)C(O)R$^{25}$, —N(R$^{24}$)S(O)R$^{25}$, —N(R$^{24}$)S(O)$_2$R$^{25}$, —CH$_2$—N(R$^{24}$)S(O)$_2$R$^{25}$, —N(R$^{24}$)S(O)$_2$N(R$^{25}$)(R$^{26}$), —N(R$^{24}$)S(O)N(R$^{25}$)(R$^{26}$), —N(R$^{24}$)C(O)N(R$^{25}$)(R$^{26}$), —CH$_2$—N(R$^{24}$)C(O)N(R$^{25}$)(R$^{26}$), —N(R$^{24}$)C(O)OR$^{25}$, —CH$_2$—N(R$^{24}$)C(O)OR$^{25}$, —S(O)R$^{24}$ and —S(O)$_2$R$^{24}$;

$R^{24}$, $R^{25}$ and $R^{26}$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, $R^{27}$-alkyl, $R^{27}$-arylalkyl, $R^{27}$-heteroarylalkyl, $R^{27}$-cycloalkylalkyl, $R^{27}$-heterocycloalkylalkyl, $R^{27}$-arylcycloalkylalkyl, $R^{27}$-heteroarylcycloalkylalkyl, $R^{27}$-arylheterocycloalkylalkyl, $R^{27}$-heteroarylheterocycloalkylalkyl, $R^{27}$-cycloalkyl, $R^{27}$-arylcycloalkyl, $R^{27}$-heteroarylcycloalkyl, $R^{27}$-heterocycloalkyl, $R^{27}$-arylheterocycloalkyl, $R^{27}$-heteroarylheterocycloalkyl, $R^{27}$-alkenyl, $R^{27}$-arylalkenyl, $R^{27}$-cycloalkenyl, $R^{27}$-arylcycloalkenyl, $R^{27}$-heteroarylcycloalkenyl, $R^{27}$-heterocycloalkenyl, $R^{27}$-arylheterocycloalkenyl, $R^{27}$-heteroarylheterocycloalkenyl, $R^{27}$-alkynyl, $R^{27}$-arylalkynyl, $R^{27}$-aryl, $R^{27}$-cycloalkylaryl, $R^{27}$-heterocycloalkylaryl, $R^{27}$-cycloalkenylaryl, $R^{27}$-heterocycloalkenylaryl, $R^{27}$-heteroaryl, $R^{27}$-cycloalkylheteroaryl, $R^{27}$-heterocycloalkylheteroaryl, $R^{27}$-cycloalkenylheteroaryl and $R^{27}$-heterocycloalkenylheteroaryl;

$R^{27}$ is 1-5 substituents independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —NO$_2$, halo, —CF$_3$, —CN, alkyl-CN, —C(O)R$^{28}$, —C(O)OH, —C(O)OR$^{28}$, —C(O)NHR$^{29}$, —C(O)N(alkyl)$_2$, —C(O)N(alkyl)(aryl), —C(O)N(alkyl)(heteroaryl), —SR$^{28}$, —S(O)$_2$R$^{29}$, —S(O)NH$_2$, —S(O)NH(alkyl), —S(O)N(alkyl)(alkyl), —S(O)NH(aryl), —S(O)$_2$NH$_2$, —S(O)$_2$NHR$^{28}$, —S(O)$_2$NH(aryl), —S(O)$_2$NH(heterocycloalkyl), —S(O)$_2$N(alkyl)$_2$, —S(O)$_2$N(alkyl)(aryl), —OH, —OR$^{29}$, —O-heterocycloalkyl, —O-cycloalkylalkyl, —O-heterocycloalkylalkyl, —NH$_2$, —NHR$^{29}$, —N(alkyl)$_2$, —N(arylalkyl)$_2$, —N(arylalkyl)(heteroarylalkyl), —NHC(O)R$^{29}$, —NHC(O)NH$_2$, —NHC(O)NH(alkyl), —NHC(O)N(alkyl) (alkyl), —N(alkyl)C(O)NH(alkyl), —N(alkyl)C(O)N(alkyl) (alkyl), —NHS(O)$_2$R$^{29}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

R$^{28}$ is alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl;

R$^{29}$ is alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl;

R$^{30}$ is independently selected from the group consisting of alkylene, arylalkylene, heteroarylalkylene, cycloalkylalkylene, heterocycloalkylalkylene, arylcycloalkylalkylene, heteroarylcycloalkylalkylene, arylheterocycloalkylalkylene, heteroarylheterocycloalkylalkylene, cycloalkylene, arylcycloalkylene, heteroarylcycloalkylene, heterocycloalkylene, arylheterocycloalkylene, heteroarylheterocycloalkylene, alkenylene, arylalkenylene, cycloalkenylene, arylcycloalkenylene, heteroarylcycloalkenylene, heterocycloalkenylene, arylheterocycloalkenylene, heteroarylheterocycloalkenylene, alkynylene, arylalkynylene, arylene, cycloalkylarylene, heterocycloalkylarylene, cycloalkenylarylene, heterocycloalkenylarylene, heteroarylene, cycloalkylheteroarylene, heterocycloalkylheteroarylene, cycloalkenylheteroarylene and heterocycloalkenylheteroarylene, wherein each of said R$^{30}$ groups is independently unsubstituted or substituted at 1 to 3 hydrogens by 1 to 3 R$^{21}$ groups; and R$^{31}$ is

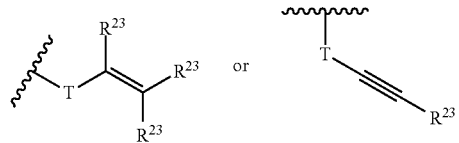

wherein T is a bond, —O—((C(R$^{23}$)(R$^{23}$))—, —S—((C(R$^{23}$)(R$^{23}$))—, —N—((C(R$^{23}$)(R$^{23}$))— or —((C(R$^{23}$)(R$^{23}$))$_{1-3}$—.

In another aspect, the invention relates to a pharmaceutical composition comprising at least one compound of formula I and a pharmaceutically acceptable carrier.

In another aspect, the invention comprises the method of inhibiting aspartyl proteases comprising administering at least one compound of formula I to a patient in need of such treatment.

More specifically, the invention comprises: the method of treating a cardiovascular disease such as hypertension, renal failure, congestive heart failure or another disease modulated by renin inhibition; the method of treating Human Immunodeficiency Virus; the method of treating a cognitive or neurodegenerative disease such as Alzheimer's Disease; the method of inhibiting plasmepsins I and II for treatment of malaria; the method of inhibiting Cathepsin D for the treatment of Alzheimer's Disease, breast cancer, and ovarian cancer; and the method of inhibiting protozoal enzymes, for example inhibition of *plasmodium falciparum*, for the treatment of fungal infections. Said method of treatment comprise administering at least one compound of formula I to a patient in need of such treatment. In particular, the invention comprises the method of treating Alzheimer's Disease comprising administering at least one compound of formula I to a patient in need of such treatment.

In another aspect, the invention comprises the method of treating Alzheimer's Disease comprising administering to a patient in need of such treatment a combination of at least one compound of formula I and a cholinesterase inhibitor or a muscarinic m$_1$ agonist or m$_2$ antagonist.

In a final aspect, the invention relates to a kit comprising in separate containers in a single package pharmaceutical compositions for use in combination, in which one container comprises a compound of formula I in a pharmaceutically acceptable carrier and a second container comprises a cholinesterase inhibitor or a muscarinic m$_1$ agonist or m$_2$ antagonist in a pharmaceutically acceptable carrier, the combined quantities being an effective amount to treat a cognitive disease or neurodegenerative disease such as Alzheimer's Disease.

DETAILED DESCRIPTION

In general, it is understood that divalent groups are to be read left to right.

Preferred compounds of formula I include the following structures:

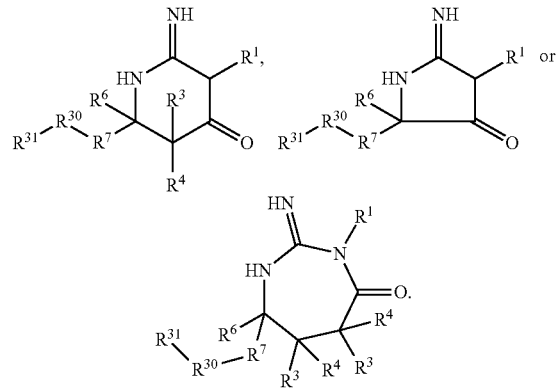

Preferred compounds of formula I are those compounds wherein R$^1$ is H, alkyl, arylalkyl, heteroarylalkyl, cycloalkylalkyl, heterocylocalkylalkyl or cycloalkyl or more preferably.

Another group of preferred compounds of formula I are those compounds wherein R$^2$ is H.

Preferred compounds of formula I are those compounds wherein $R^3$ is H, alkyl, aryl, aryl substituted with 1 to 5 $R^{21}$ groups, heteroaryl, heteroaryl substituted with 1 to 5 $R^{21}$ groups, cycloalkyl, heterocycloalkyl, halo, —$OR^9$, cycloalkyl, or —$SR^{19}$ or more preferably, $R^3$ is H, —$CH_3$, F, Cl, Br, —$OCH_3$, —$SCH_3$,

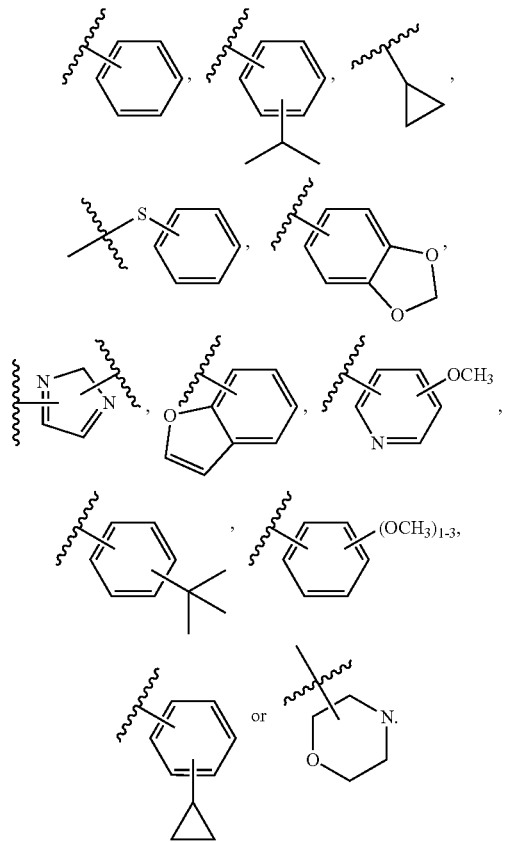

Preferred compounds of the invention are those of formula I wherein $R^4$ is H, alkyl, aryl, aryl substituted with 1 to 5 $R^{21}$ groups, heteroaryl, heteroaryl substituted with 1 to 5 $R^{21}$ groups, cycloalkyl, heterocycloalkyl, halo, —$OR^9$, cycloalkyl, or —$SR^{19}$, or more preferably $R^4$ is H, —$CH_3$, F, Cl, Br, —$OCH_3$, —$SCH_3$,

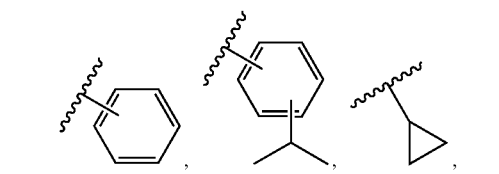

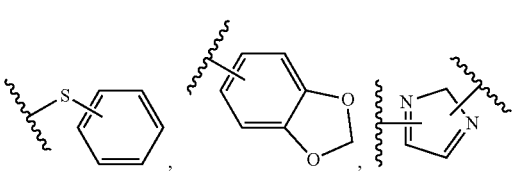

-continued

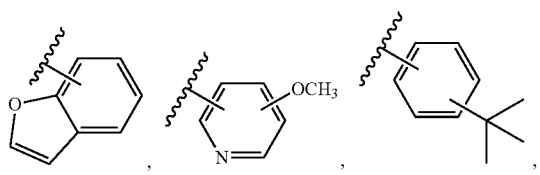

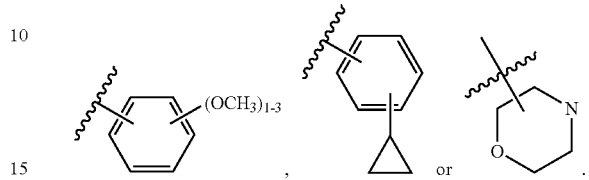

More preferred compounds of formula I are those compounds wherein W is —C(O)— or X is —N($R^5$)—, or more preferably $R^5$ is H.

Another group of preferred compounds of formula I are those compounds wherein $R^6$ is H, alkyl, cycloalkyl or cycloalkylalkyl or more preferably, $R^6$ is —$CH_3$ or

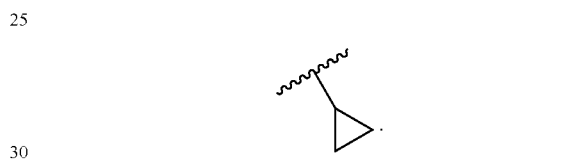

Preferred compounds of formula I are those compounds wherein $R^7$ is arylene, heteroarylene, cycloalkylene, heterocycloalkylene or alkylene, wherein each of said $R^7$ groups is independently unsubstituted or substituted at 1 to 3 hydrogens by 1 to 3 $R^{21}$ groups; or more preferably, $R^7$ is

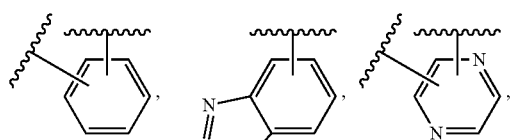

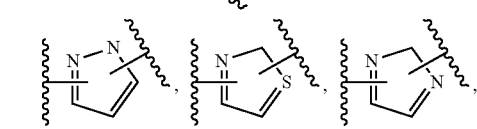

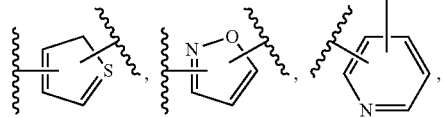

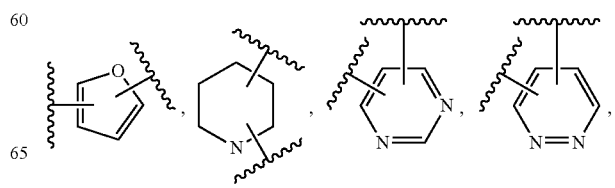

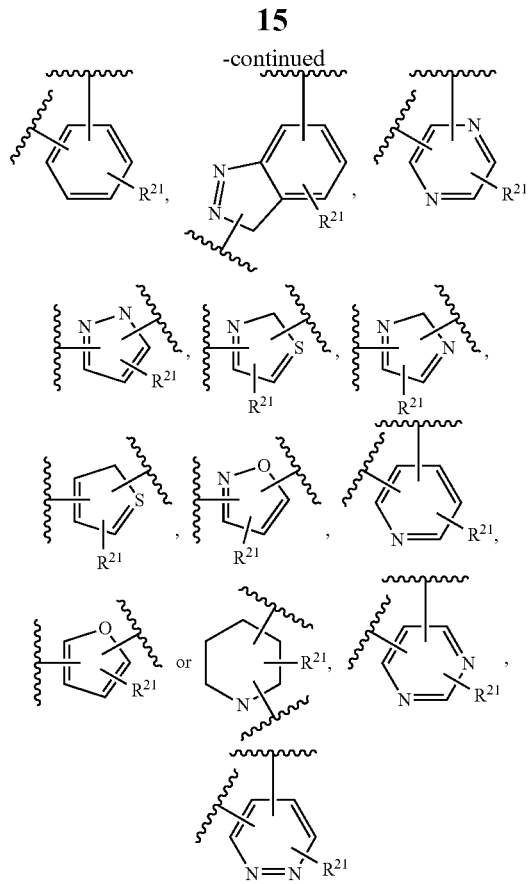

and R$^{21}$ is —CN, —NO$_2$, NH$_2$, —CH$_3$ or halo.

Another group of preferred compounds of formula I are those compounds wherein R$^6$ and R$^7$ are combined to form

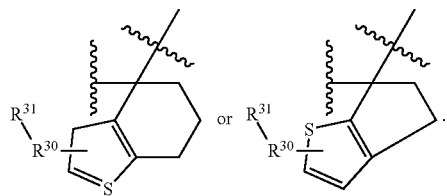

An even further group of preferred compounds of formula I are those compounds wherein R$^{30}$ is arylene, heteroarylene, cycloalkylene, heterocycloalkylene or alkylene, wherein each of said R$^{30}$ groups is independently unsubstituted or substituted at 1 to 3 hydrogens by 1 to 3 R$^{21}$ groups; or more preferably R$^{30}$ is

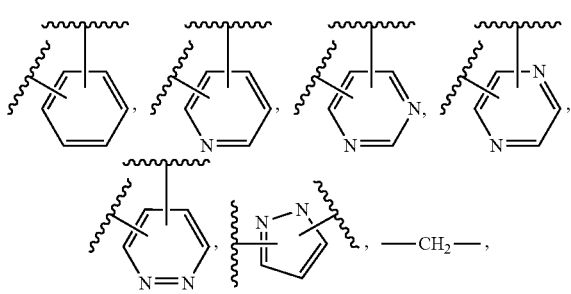

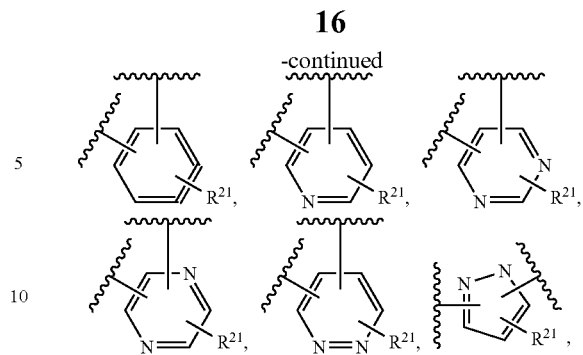

wherein R$^{21}$ is —CN, —NO$_2$, NH$_2$, —CH$_3$ or halo.

Another group of preferred compounds of formula I are those compounds wherein T is a bond or —CH$_2$—.

Another group of preferred compounds of formula I are those compounds wherein R$^{31}$ is

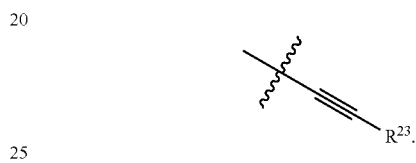

Another group of preferred compounds of formula I those compounds wherein R$^{23}$ is H, alkyl, alkyl substituted with 1 to 5 R$^{27}$ groups, cycloalkyl, aryl, heteroaryl, cycloalkyl substituted with 1 to 5 R$^{27}$ groups, aryl substituted with 1 to 5 R$^{27}$ groups or heteroaryl substituted with 1 to 5 R$^{27}$ groups.

Another group of preferred compounds of formula I are those compounds wherein

W is —C(O)—;
X is —N(R$^5$)—;
R$^1$ is H, alkyl, arylalkyl, heteroarylalkyl, cycloalkylalkyl, heterocylocalkylalkyl or cycloalkyl;
R$^2$ is H;
R$^5$ is H;
R$^3$ is H, alkyl, aryl, aryl substituted with 1 to 5 R$^{21}$ groups, heteroaryl, heteroaryl substituted with 1 to 5 R$^{21}$ groups, cycloalkyl, heterocycloalkyl, halo, —OR$^9$, cycloalkyl, or —SR$^{19}$;
R$^4$ is H, alkyl, aryl, aryl substituted with 1 to 5 R$^{21}$ groups, heteroaryl, heteroaryl substituted with 1 to 5 R$^{21}$ groups, cycloalkyl, heterocycloalkyl, halo, —OR$^9$, cycloalkyl, or —SR$^{19}$;
R$^6$ is H, alkyl, cycloalkyl or cycloalkylalkyl;
R$^7$ is arylene, heteroarylene, cycloalkylene, heterocloalkylene or alkylene, wherein each of said R$^7$ groups is independently unsubstituted or substituted at 1 to 3 hydrogens by 1 to 3 R$^{21}$ groups;
or R$^6$ and R$^7$ are combined to form

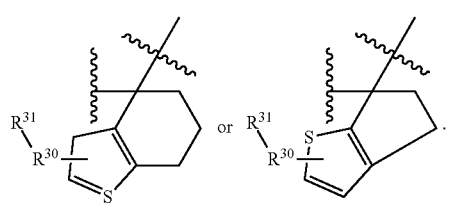

R$^{30}$ is arylene, heteroarylene, cycloalkylene, heterocycloalkylene or alkylene, wherein each of said R$^{30}$ groups is independently unsubstituted or substituted at 1 to 3 hydrogens by 1 to 3 R$^{21}$ groups;

T is a bond or —CH$_2$—;

R$^{31}$ is

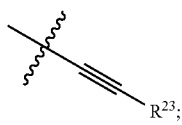

and

R$^{23}$ is H, alkyl, alkyl substituted with 1 to 5 R$^{27}$ groups, cycloalkyl, aryl, heteroaryl, cycloalkyl substituted with 1 to 5 R$^{27}$ groups, aryl substituted with 1 to 5 R$^{27}$ groups or heteroaryl substituted with 1 to 5 R$^{27}$ groups.

Another group of preferred compounds of formula I are those compounds wherein R$^3$ is H, —CH$_3$, F, Cl, Br, —OCH$_3$, —SCH$_3$,

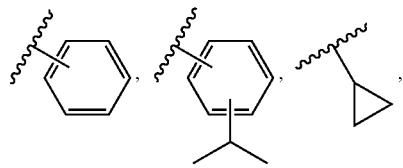

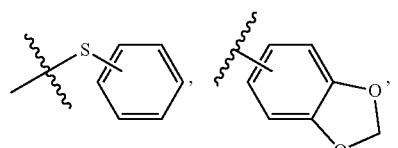

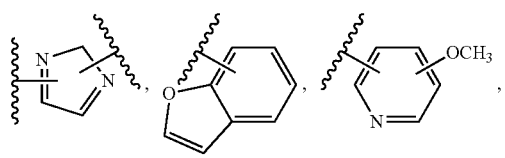

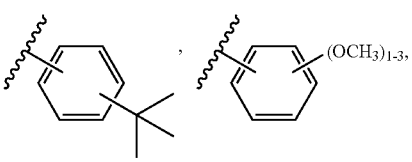

R$^4$ is H, —CH$_3$, F, Cl, Br, —OCH$_3$, —SCH$_3$,

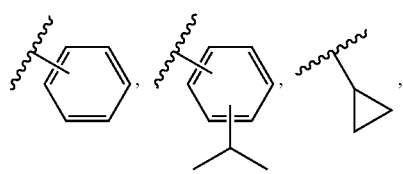

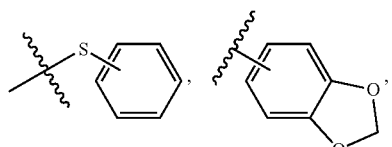

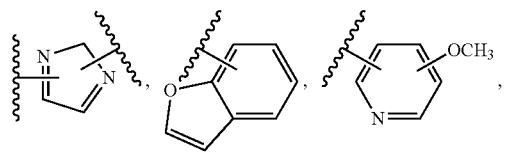

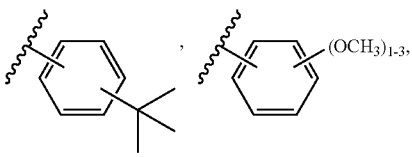

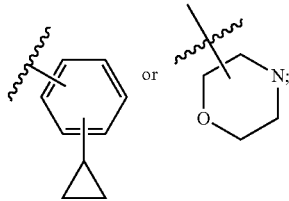

R$^6$ is —CH$_3$ or

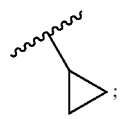

R$^7$ is

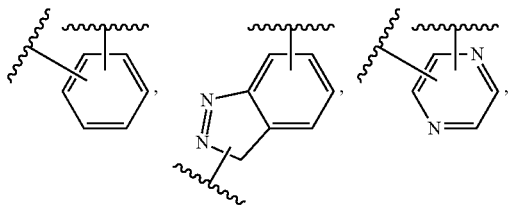

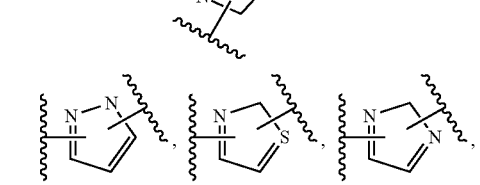

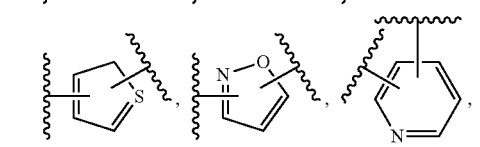

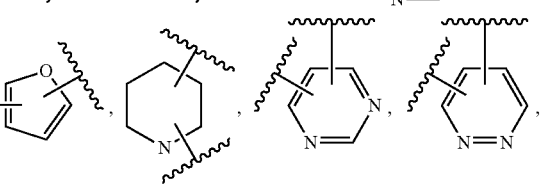

-continued

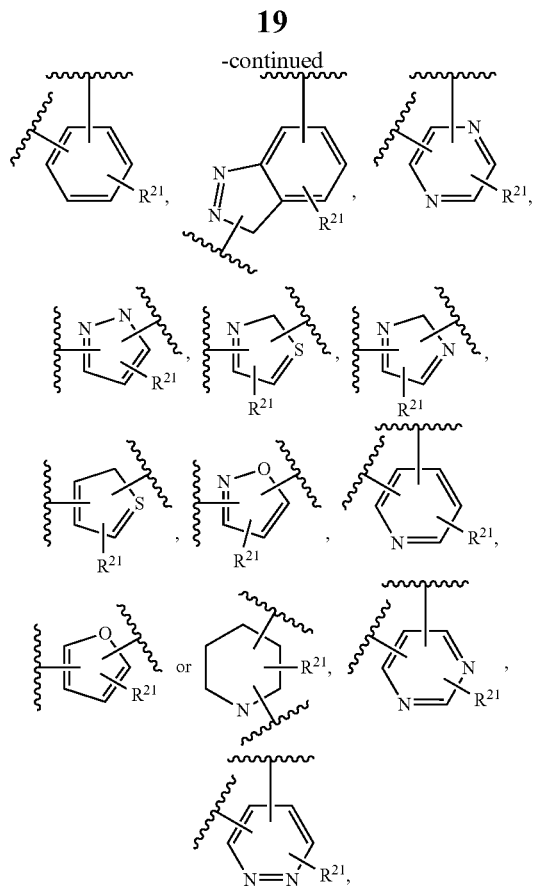

wherein R²¹ is —CN, —NO₂, NH₂, —CH₃ or halo;
or R⁶ and R⁷ are combined to form

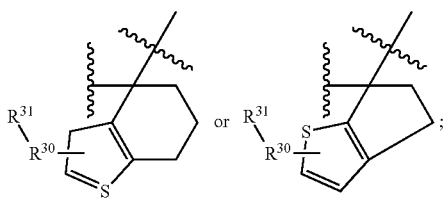

R³⁰ is

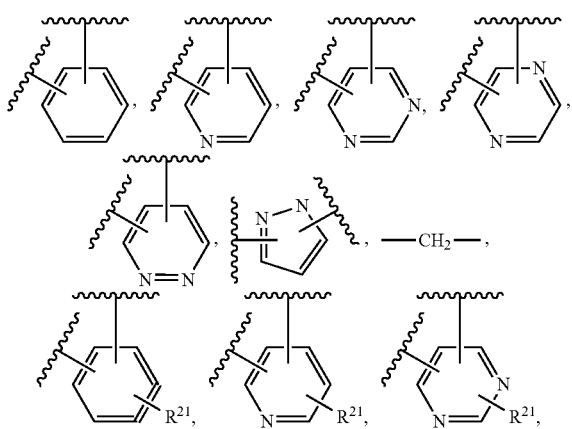

-continued

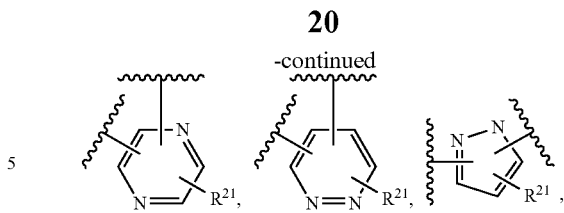

wherein $R^{21}$ is —CN, —NO$_2$, NH$_2$, —CH$_3$ or halo; and $R^{23}$ is H, —CH$_3$, —CF$_3$, —CH$_2$—O—CH$_3$, —CH$_2$—CH$_2$—CH$_3$, —CH$_2$—CH$_2$—(CH)—(CH$_3$)$_2$,

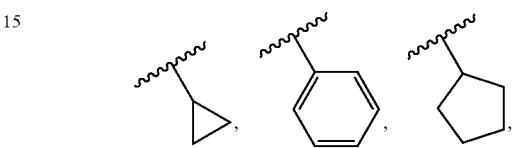

or —CH—(CH$_3$)$_2$.

The compounds of Formula (I), or pharmaceutically acceptable salts, solvates, or esters thereof, are preferably purified to a degree suitable for use as a pharmaceutically active substance. That is, the compounds of Formula (I) can have a purity of 95 wt % or more (excluding adjuvants such as pharmaceutically acceptable carriers, solvents, etc., which are used in formulating the compound of Formula (I) into a conventional form, such as a pill, capsule, IV solution, etc. suitable for administration into a patient). In other embodiments, the purity can be 97 wt % or more, or 99 wt % or more. A purified compound of Formula (I) includes a single isomer having a purity, as discussed above, of 95 wt % or more, 97 wt % or more, or 99 wt % or more, as discussed above.

Alternatively, the purified compound of Formula (I) can include a mixture of isomers, each having a structure according to Formula (I), where the amount of impurity (i.e., compounds or other contaminants, exclusive of adjuvants as discussed above) is 5 wt % or less, 3 wt % or less, or 1 wt % or less. For example, the purified compound of Formula (I) can be an isomeric mixture of compounds, where the ratio of the amounts of the two isomers is approximately 1:1, and the combined amount of the two isomers is 95 wt % or more, 97 wt % or more, or 99 wt % or more.

It is noted that the carbons of formula I may be replaced with 1 to 3 silicon atoms so long as all valency requirements are satisfied.

As used above, and throughout the specification, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. Non-limiting examples of suitable alkyl groups include methyl, ethyl, n-propyl, isopropyl, n-butyl, t-butyl, n-pentyl, heptyl, nonyl and decyl. $R^{21}$-substituted alkyl groups include fluoromethyl, trifluoromethyl and cyclopropylmethyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl.

"Aryl" means an aromatic monocyclic or multicyclic ring system comprising about 6 to about 14 carbon atoms, preferably about 6 to about 10 carbon atoms. The aryl group can be optionally substituted with one or more substituents (e.g., $R^{18}$, $R^{21}$, $R^{22}$, etc.) which may be the same or different, and are as defined herein or two substituents on adjacent carbons can be linked together to form

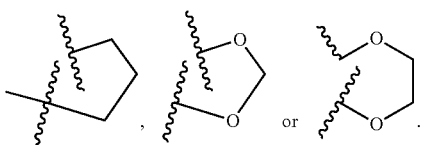

Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one to four of the ring atoms is an element other than carbon, for example nitrogen, oxygen or sulfur, alone or in combination. Preferred heteroaryls contain about 5 to about 6 ring atoms. The "heteroaryl" can be optionally substituted by one or more $R^{21}$ substituents which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Cycloalkyl" means a non-aromatic mono- or multicyclic ring system comprising about 3 to about 15 carbon atoms, preferably about 5 to about 10 carbon atoms. Preferred cycloalkyl rings contain about 5 to about 7 ring atoms. The cycloalkyl can be optionally substituted with one or more $R^{21}$ substituents which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like. Further non-limiting examples of cycloalkyl include the following

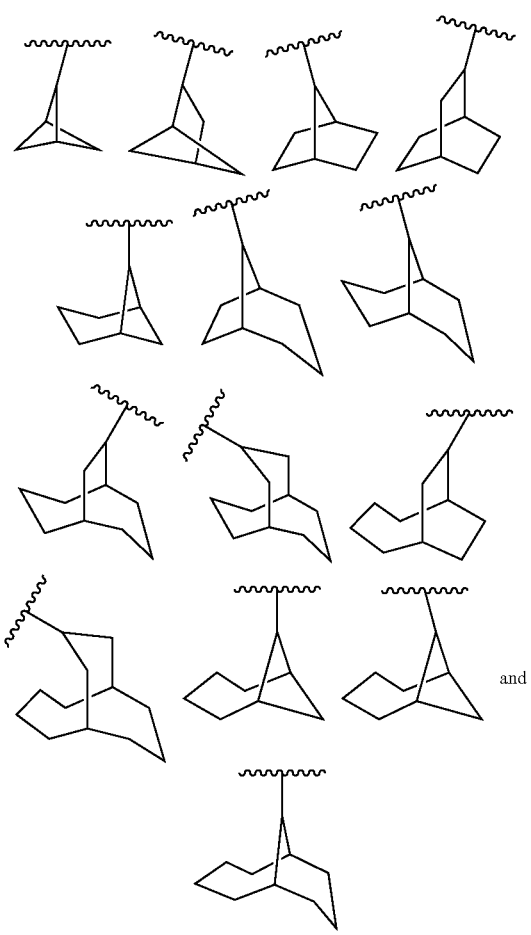

"Cycloalkylether" means a non-aromatic ring of 3 to 15 atoms comprising an oxygen atom and 2 to 14 carbon atoms. Ring carbon atoms can be substituted, provided that substituents adjacent to the ring oxygen do not include halo or substituents joined to the ring through an oxygen, nitrogen or sulfur atom.

"Cycloalkenyl" means a non-aromatic mono or multicyclic ring system comprising about 3 to about 15 carbon atoms, preferably about 5 to about 10 carbon atoms which contains at least one carbon-carbon double bond. The cycloalkenyl ring can be optionally substituted with one or more $R^{21}$ substituents which may be the same or different, and are as defined above. Preferred cycloalkenyl rings contain about 5 to about 7 ring atoms. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclenyl" (or "heterocycloalkenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridyl, 1,2-dihydropyridyl, 1,4-dihydropyridyl, 1,2,3,6-tetrahydropyridyl, 1,4,5,6-tetrahydropyrimidyl, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Halo" means fluoro, chloro, bromo, or iodo groups. Preferred are fluoro, chloro or bromo, and more preferred are fluoro and chloro.

"Haloalkyl" means an alkyl as defined above wherein one or more hydrogen atoms on the alkyl is replaced by a halo group defined above.

"Heterocyclyl" or "Heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" can also mean a heterocyclyl wherein a single moiety (e.g., carbonyl) can simultaneously replace two available hydrogens on the same carbon atom on a ring system. Example of such moiety is pyrrolidone:

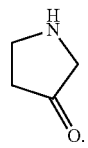

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

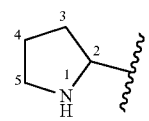

there is no —OH attached directly to carbons marked 2 and 5

"Arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Arylcycloalkyl" means a group derived from a fused aryl and cycloalkyl as defined herein. Preferred arylcycloalkyls are those wherein aryl is phenyl and cycloalkyl consists of about 5 to about 6 ring atoms. The arylcycloalkyl can be optionally substituted by 1-5 $R^{21}$ substituents. Non-limiting examples of suitable arylcycloalkyls include indanyl and 1,2,3,4-tetrahydronaphthyl and the like. The bond to the parent moiety is through a non-aromatic carbon atom.

"Arylheterocycloalkyl" means a group derived from a fused aryl and heterocycloalkyl as defined herein. Preferred arylcycloalkyls are those wherein aryl is phenyl and heterocycloalkyl consists of about 5 to about 6 ring atoms. The arylheterocycloalkyl can be optionally substituted by 1-5 $R^{21}$ substituents. Non-limiting examples of suitable arylheterocycloalkyls include

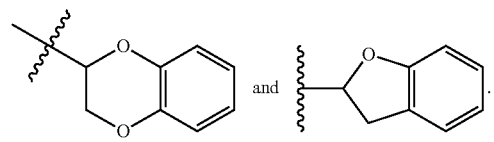 [SMILES: *C1COc2ccccc2O1 ; *C1Cc2ccccc2O1]

The bond to the parent moiety is through a non-aromatic carbon atom.

Similarly, "heteroarylalkyl" "cycloalkylalkyl" and "heterocycloalkylalkyl" mean a heteroaryl-, cycloalkyl- or heterocycloalkyl-alkyl-group in which the heteroaryl, cycloalkyl, heterocycloalkyl and alkyl are as previously described. It is also understood that the terms "arylcycloalkylalkyl", "heteroarylcycloalkylalkyl", "arylheterocycloalkylalkyl", "heteroarylheterocycloalkylalkyl", "heteroarylcycloalkyl", "heteroarylheterocycloalkyl", "arylcycloalkenyl", "heteroarylcycloalkenyl", "heterocycloalkenyl", "arylheterocycloalkenyl", "heteroarylheterocycloalkenyl", "cycloalkylaryl", "heterocycloalkylaryl", "heterocycloalkenylaryl", "heteroarylcycloalkylheteroaryl", "cycloalkenylaryl" "cycloalkenylheteroaryl", "heterocycloalkenylaryl" and "heterocycloalkenylheteroaryl" similarly represented by the combination of the groups aryl-, cycloalkyl-, alkyl-, heteroaryl-, heterocycloalkyl-, cycloalkenyl- and heterocycloalkenyl- as previously described. Preferred groups contain a lower alkyl group. The bond to the parent moiety is through the alkyl.

"Acyl" means an H—C(O)—, alkyl-C(O)—, alkenyl-C(O)—, alkynyl-C(O)— or cycloalkyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Alkoxyalkyl" means a group derived from an alkoxy and alkyl as defined herein. The bond to the parent moiety is through the alkyl.

"Arylalkenyl" means a group derived from aryl and alkenyl as defined herein. Preferred arylalkenyls are those wherein aryl is phenyl and the alkenyl consists of about 3 to about 6 atoms. The arylalkenyl can be optionally substituted by one or more $R^{21}$ substituents. The bond to the parent moiety is through a non-aromatic carbon atom.

"Arylalkynyl" means a group derived from aryl and alkynyl as defined herein. Preferred arylalkynyls are those wherein aryl is phenyl and the alkynyl consists of about 3 to about 6 atoms. The arylalkynyl can be optionally substituted by one or more $R^{21}$ substituents. The bond to the parent moiety is through a non-aromatic carbon atom.

The suffix "ene" on alkyl, aryl, heterocycloalkyl, etc. indicates a divalent moiety, e.g., —CH$_2$CH$_2$— is ethylene, and

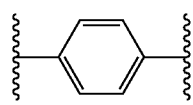

is para-phenylene. It is understood that groups ending with the suffix "ene" can be optionally substituted at least once at any of the hydrogens by $R^{21}$.

It is understood that multicyclic divalent groups, for example, arylheterocycloalkylene, can be attached to other groups via bonds that are formed on either ring of said group. For example,

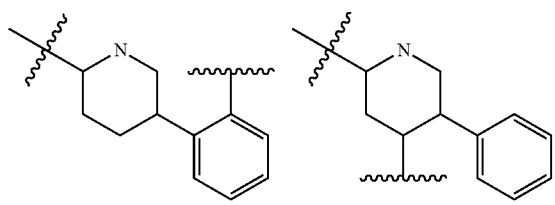

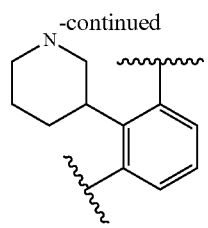

The term "optionally substituted" means optional substitution with the specified groups, radicals or moieties, in available position or positions. Substitution on a cycloalkylalkyl, heterocycloalkylalkyl, arylalkyl, or heteroarylalkyl moiety includes substitution on the ring portion and/or on the alkyl portion of the group.

When a variable appears more than once in a group, e.g., $R^8$ in —N═C(R$^8$)$_2$, or a variable appears more than once in the structure of formula I, e.g., $R^{15}$ may appear in both $R^1$ and $R^3$, the variables can be the same or different.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art. With respect to the compositions and methods comprising the use of "at least one compound of formula I," one to three compounds of formula I can be administered at the same time, preferably one.

As used herein, the term "composition" is intended to encompass a product comprising the specified ingredients in the specified amounts, as well as any product which results, directly or indirectly, from combination of the specified ingredients in the specified amounts.

The wavy line ∿∿ as a bond generally indicates a mixture of, or either of, the possible isomers, e.g., containing (R)- and (S)-stereochemistry. For example,

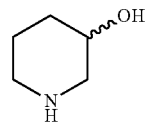

means containing both

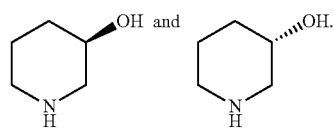 [SMILES: O[C@@H]1CCCNC1 ; O[C@H]1CCCNC1]

Lines drawn into the ring systems, such as, for example:

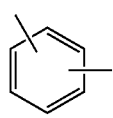

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

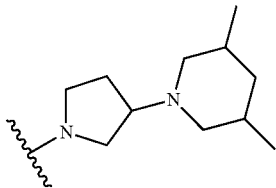 [SMILES: *N1CCC(N2CC(C)CC(C)C2)C1]

represents

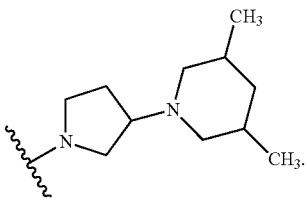 [SMILES: *N1CCC(N2CC(C)CC(C)C2)C1]

It should also be noted that any heteroatom with unsatisfied valences in the text, schemes, examples, structural formulae, and any Tables herein is assumed to have the hydrogen atom or atoms to satisfy the valences.

Those skilled in the art will recognize that certain compounds of formula I are tautomeric, and all such tautomeric forms are contemplated herein as part of the present invention. For example, said compound can be represented by any of the following structures:

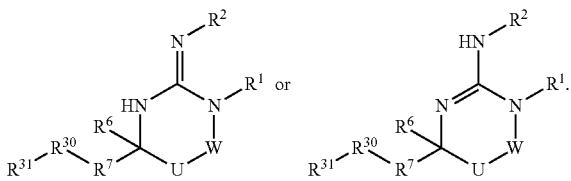

When, $R^8$, for example is, —$N(R^{15})S(O)_2N(R^{16})(R^{17})$, and $R^{16}$ and $R^{17}$ form a ring, the moiety formed, is, for example

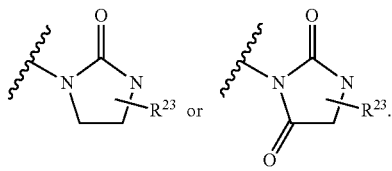

Polymorphic forms of the compounds of formula I, and of the salts, solvates and prodrugs of the compounds of formula I, are intended to be included in the present invention All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.).

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$ alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl, —$C(OH)C(O)OY^1$ wherein Y' is H, $(C_1-C_6)$alkyl or benzyl, —$C(OY^2)Y^3$ wherein $Y^2$ is $(C_1-C_4)$ alkyl and $Y^3$ is $(C_1-C_6)$alkyl, carboxy$(C_1-C_6)$alkyl, amino $(C_1-C_4)$alkyl or mono-N— or di-N,N—$(C_1-C_6)$alkylaminoalkyl, —$C(Y^4)Y^5$ wherein $Y^4$ is H or methyl and $Y^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect. "Effective amount" or "therapeutically effective amount" can also further describe an amount of compound or a composition of the present invention effective in inhibiting aspartyl protease and/or inhibiting BACE-1 and thus producing the desired therapeutic effect in a suitable patient.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, bisulfates, sulfates, sulfonates (such as those mentioned herein), tartarates, thiocyanates, toluenesulfonates (also known as tosylates,) undecanoates, and the like.

Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Phar-* maceutics (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula I, and salts, solvates, esters and prodrugs thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I, and of the salts, solvates, esters and prodrugs of the compounds of Formula I, are intended to be included in the present invention.

The compounds according to the invention have pharmacological properties; in particular, the compounds of Formula I can be inhibitors of asparty protease.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

Compounds of formula I can be made using procedures known in the art. The following reaction schemes show typical procedures, but those skilled in the art will recognize that other procedures can also be suitable.

In the Schemes and in the Example below, the following abbreviations are used:

room temperature: r.t.
high pressure liquid chromatography: HPLC
reverse-phase HPLC: RP-HPLC
liquid chromatography mass spectrometry: LCMS
mass spectrometry: MS
polytetrafluoroethylene: PTFE
hour: h
minute: min
retention time: tR
ethyl: Et
methyl: Me
benzyl: Bn
lithium diisopropylamide: LDA
1-(3-dimethylaminopropyl)-3-ethyl carbodiimide hydrochloride: EDCl
DIEA means N,N-diisopropylethylamine
ethyl acetate: EtOAc
N,N-dimethylformamide: DMF
methanol: MeOH
Ethanol: EtOH
acetonitrile: $CH_3CN$
acetic acid: AcOH
magnesium sulfate: $MgSO_4$
copper iodide: CuI
diisopropylamine: $iPr_2NH$
Dichlorobis(triphenylphosphine)palladium: $PdCl_2(PPh_3)_2$
ammonium hydroxide: $NH_4OH$
trifluoroacetic acid: TFA
benzyloxycarbonyl: Cbz
tert-butoxycarbonyl: Boc
DCM: Dichloromethane
$TMSCHN_2$: Trimethylsilyldiazomethane
Teoc-OSu: O-Trimethylsilylethoxycarbonyl N-hydroxyl-succinate
TBAF: Tetrabutylammonium Fluoride
THF: Tetrahydrofurane
MCPBA: meta-Chloroperbenzoic acid
TsOH: Toluenesulfonic acid.
PhIO: iodosobenzene
$Pb(OAc)_4$: Lead tetra-acetate Method A Experimental (General Synthesis Scheme)

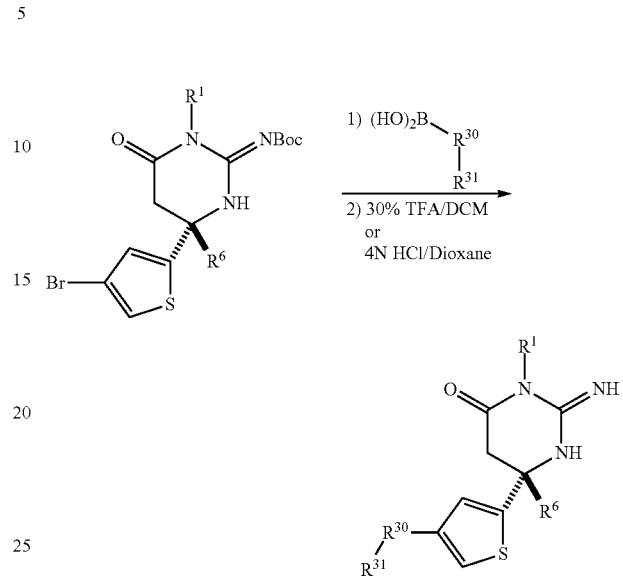

Detailed Example

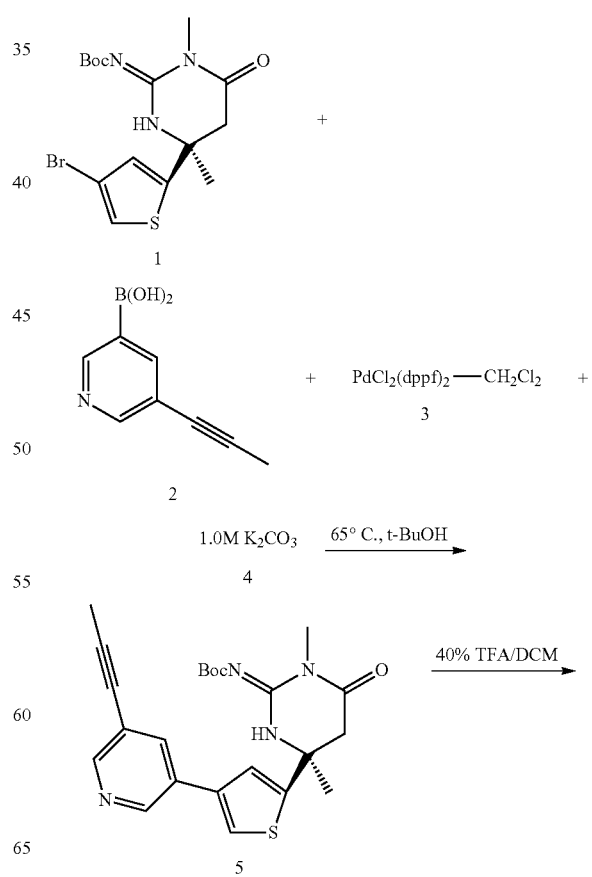

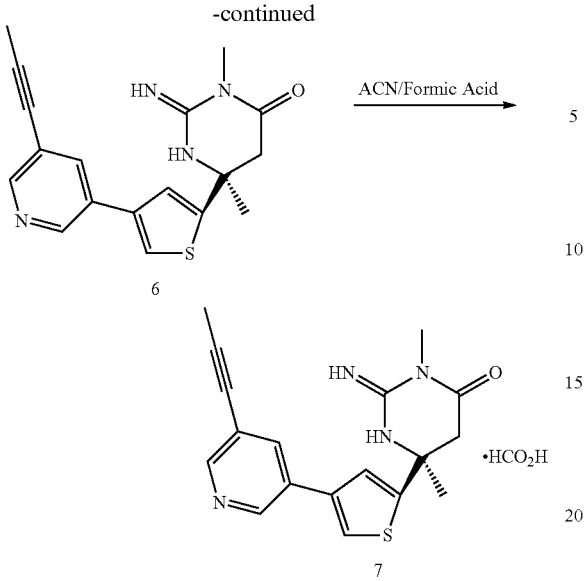

Procedure: To a round-bottomed flask fitted with reflux condenser was added 1 (20.5 g, 0.051 mol), 2 (12.3 g, 0.077 mol), 3 (1.04 g, 1.27 mmol), 4 (76.88 mL), and 80 mL t-BuOH. The reaction mixture was stirred at 65° C. for 45 minutes. After cooling to room temperature, the reaction mixture was poured to cold water and extracted by methylene chloride (6×100 mL) and dried over $Na_2SO_4$. The concentrated residue was purified by flash column chromatography (EA/H=0-80%) to afford the Boc protected compound 5 as a white solid, which was stirred for one hour in a 250 mL of 40% trifluoroacetic acid/methylene chloride solution. The solution was then concentrated and purified by flash column chromatography (7M $NH_3/CH_3OH/CH_2Cl_2$=0-5%) to afford the de-protected free form 6 as a white solid, which was dissolved in 300 mL acetonitrile and 6.78 mL formic acid and stirred for 1 hour. The solution was concentrated down and put on vacuum to afford 7 as formate salt (white solid, 18.5 g, 94% overall yield). 7: $^1$H NMR ($CD_3OD$, 400 MHz) δ 8.17 (s, 1H), 8.43 (s, 1H), 8.08 (s, 1H), 8.06 (s, 1H), 7.82 (s, 1H), 7.52 (s, 1H), 3.47 (d, 1H, J=16.8 Hz), 3.24 (d, 1H, J=16.4 Hz) 3.23 (s, 3H), 2.09 (s, 3H), 1.84 (s, 3H). MS m/z 339 (M+H)[+]. LC-MS retention time 2.32 min.

The following examples were prepared in a similar manner as the above example:

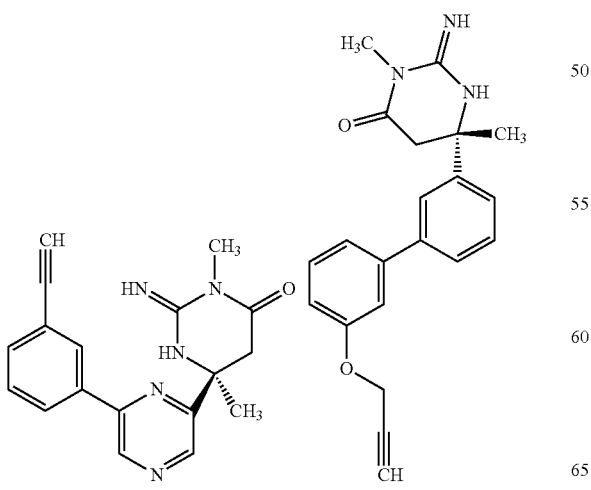

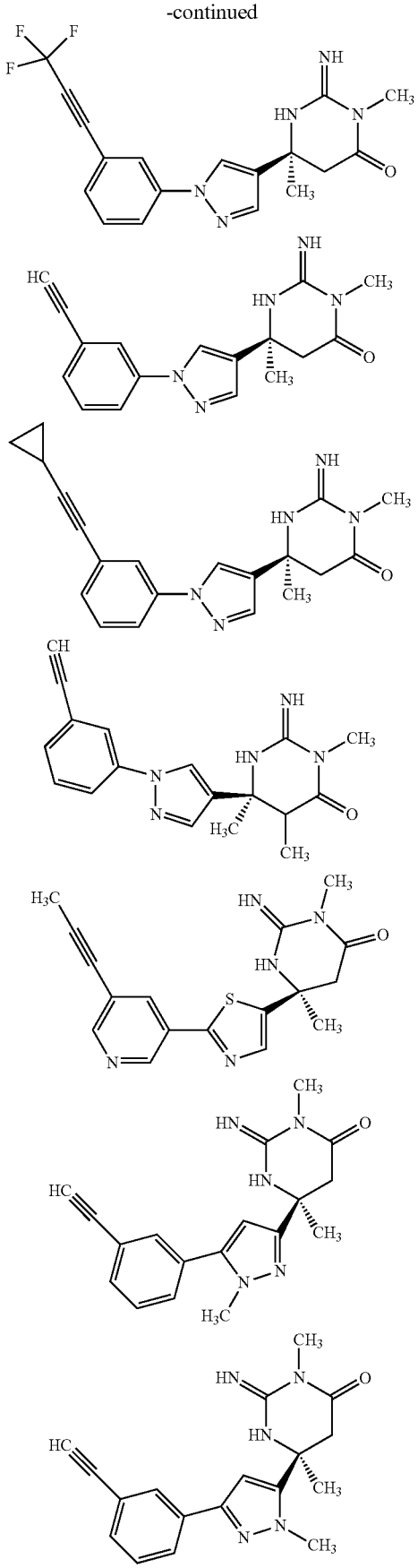

37
-continued
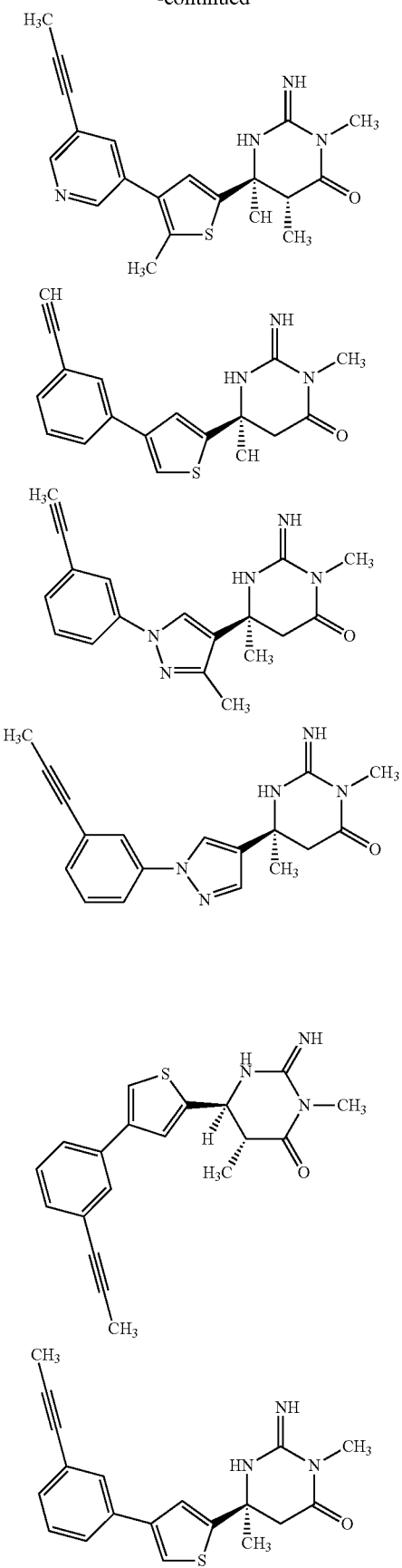
38
-continued
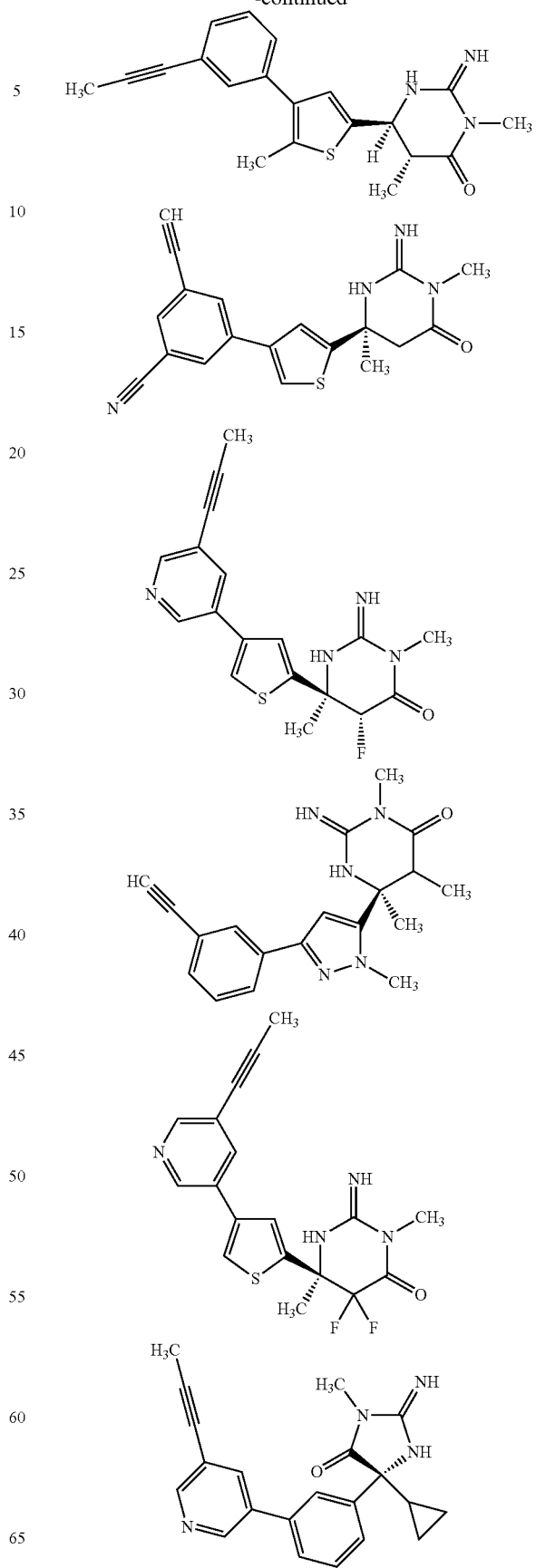

39
-continued
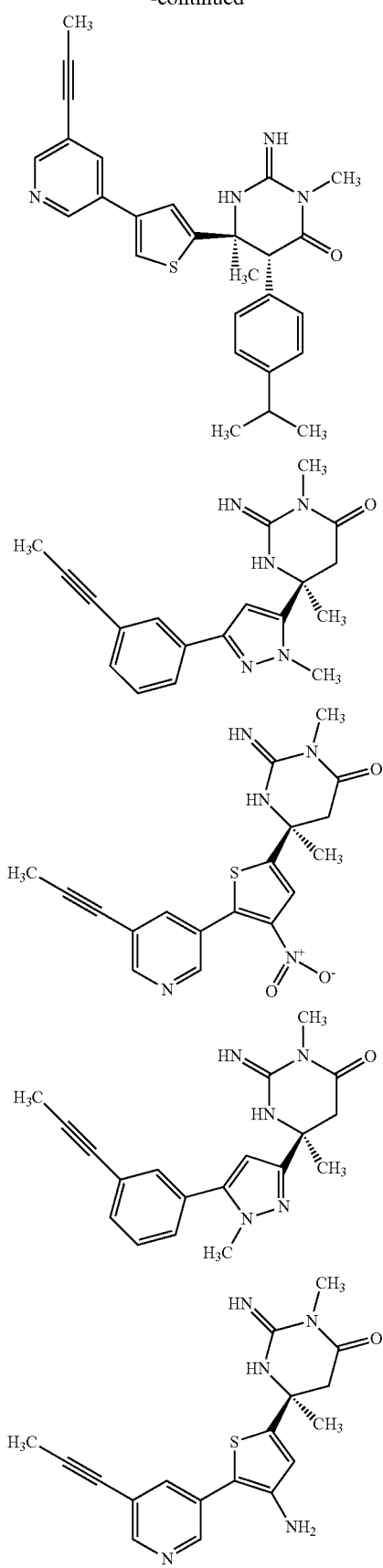
40
-continued
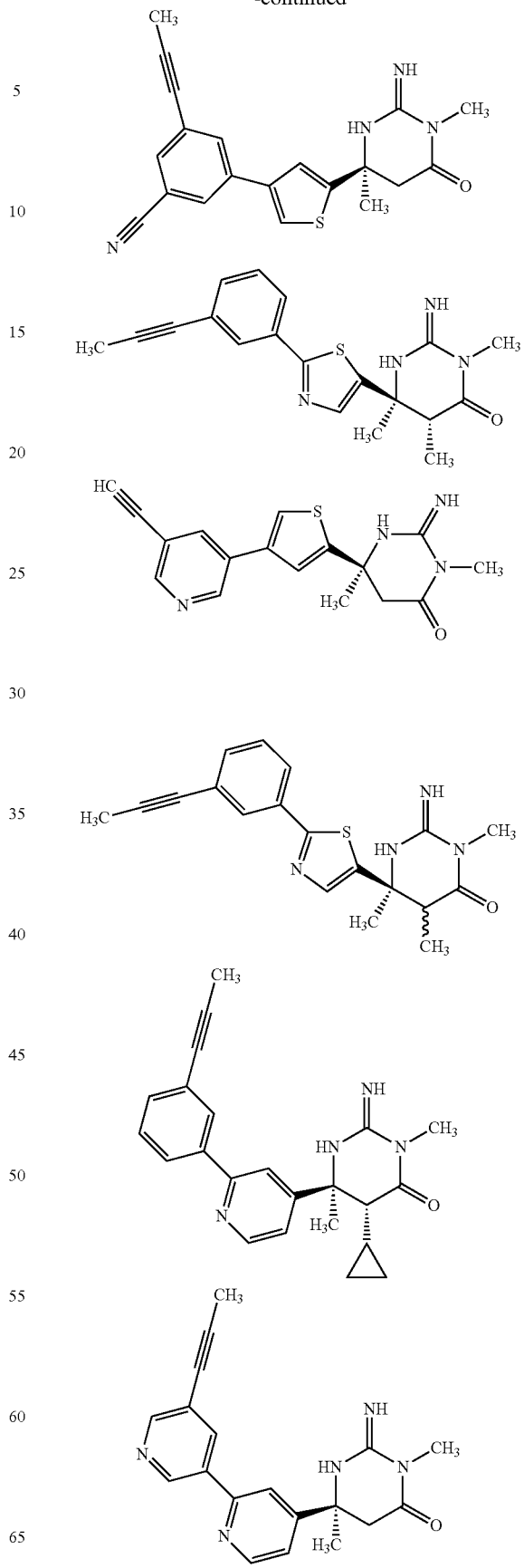

-continued
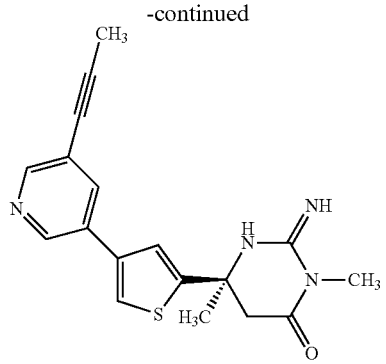
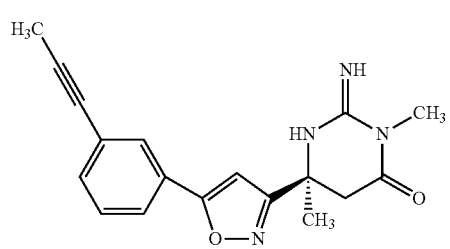
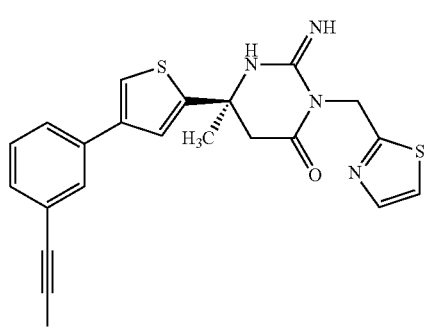
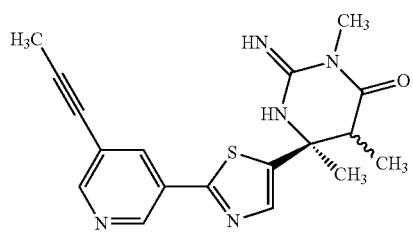
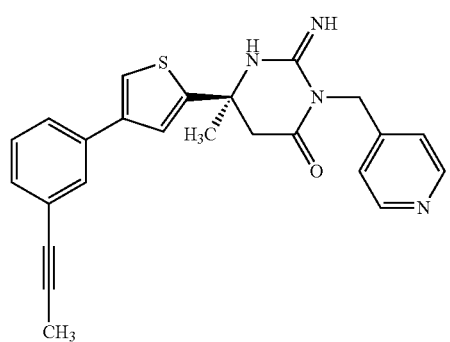
-continued
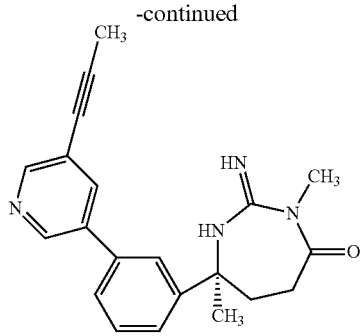
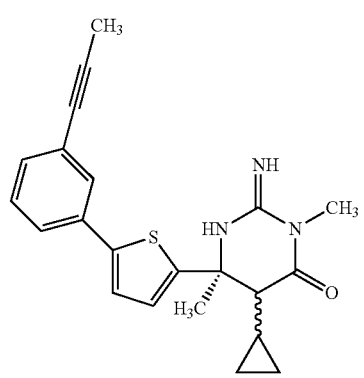
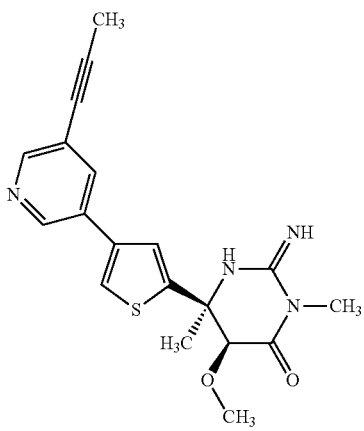
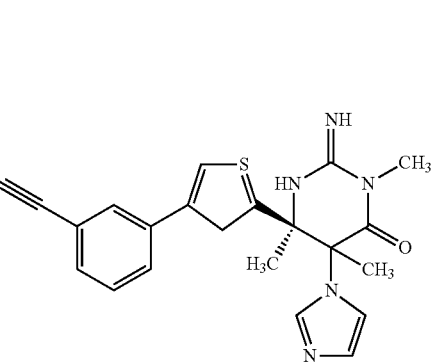

43
-continued
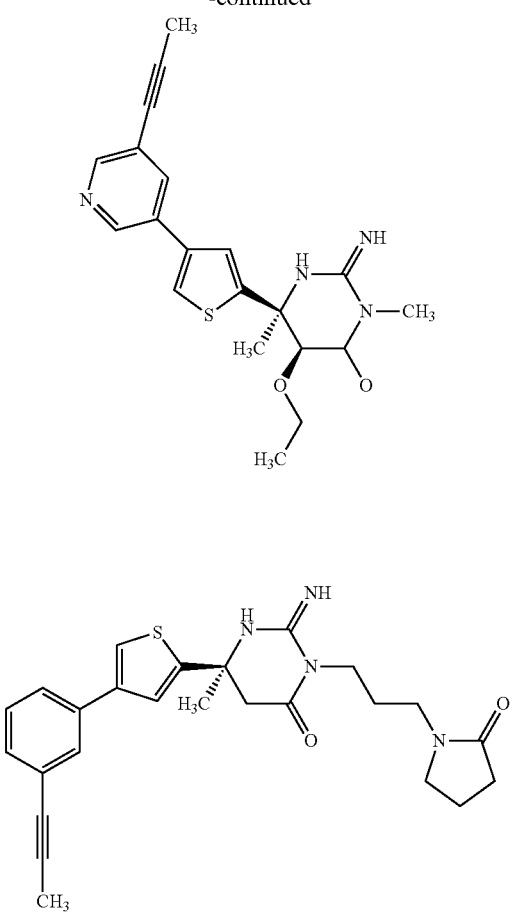
44
-continued
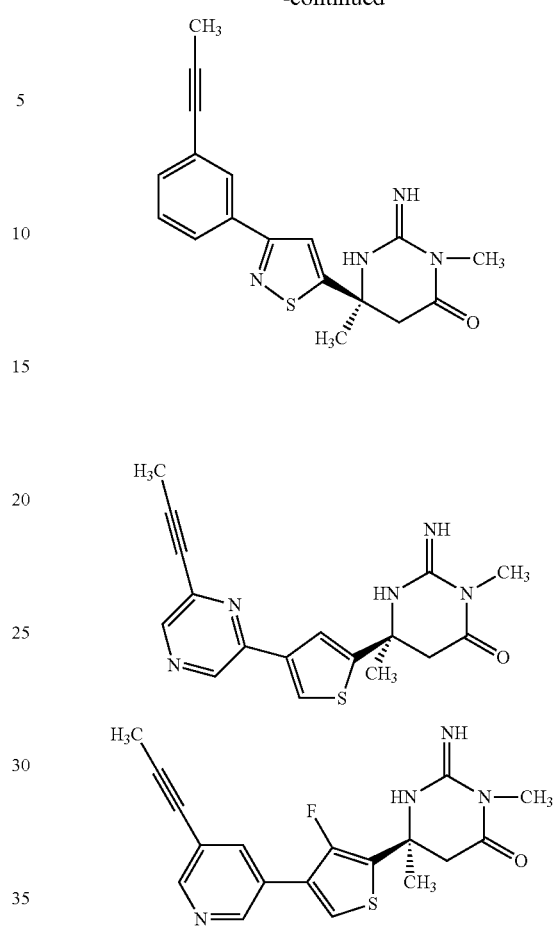
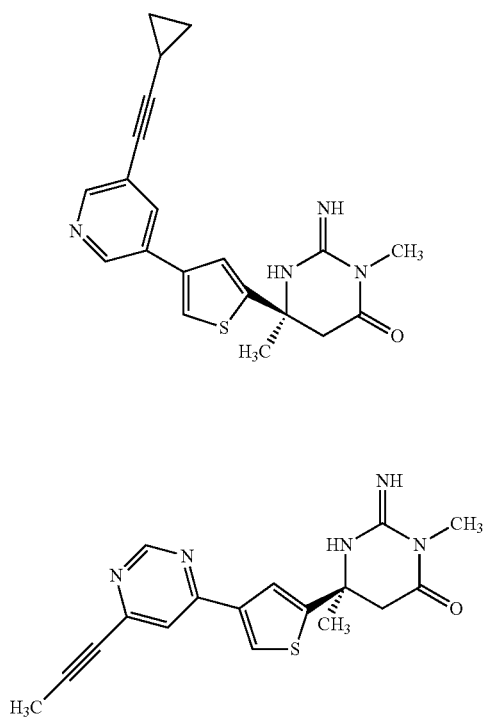
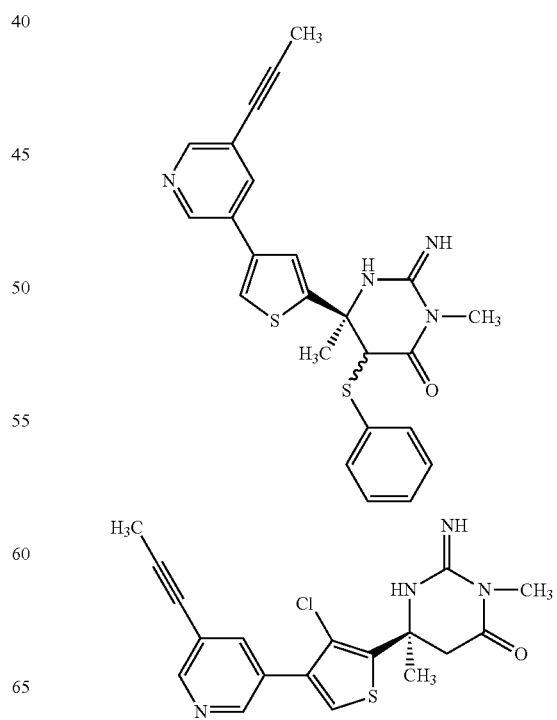

45
-continued
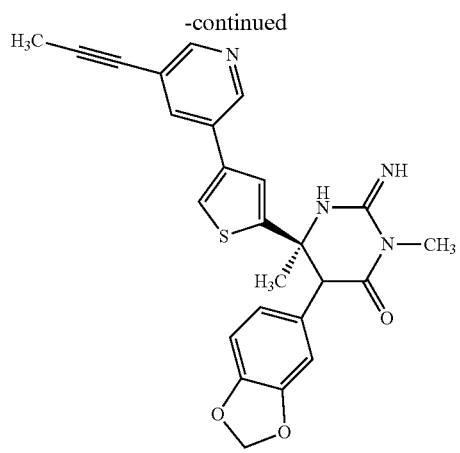
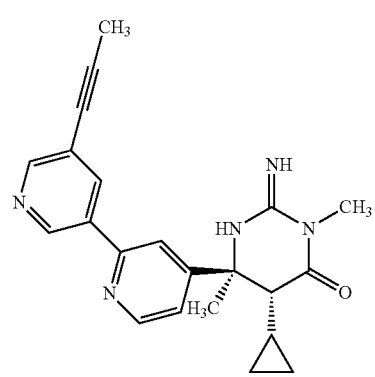
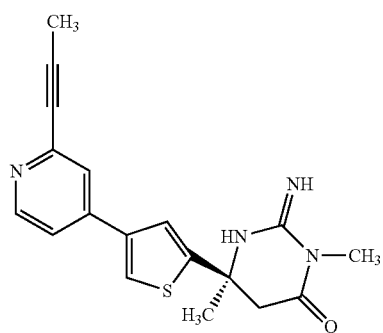
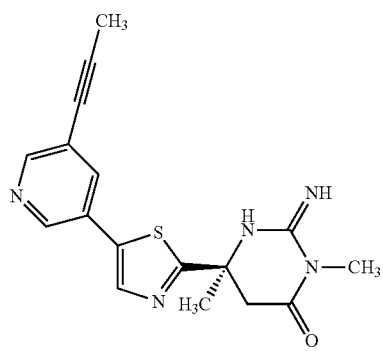
46
-continued
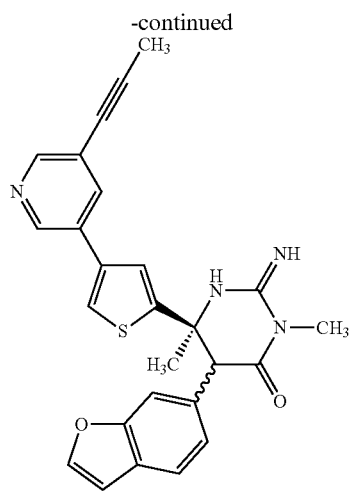
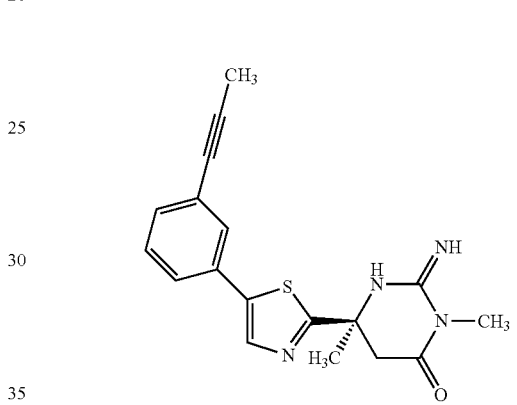
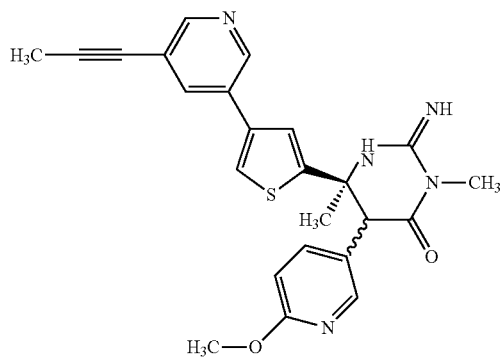
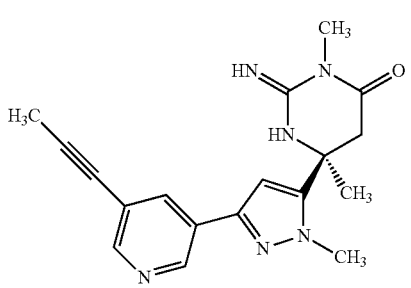

47
-continued
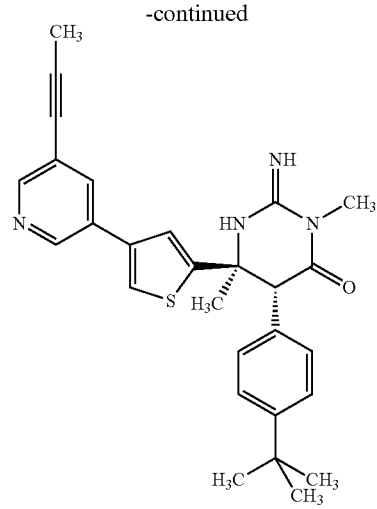
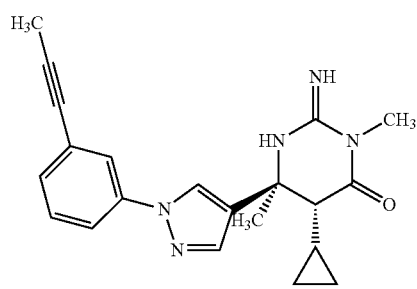
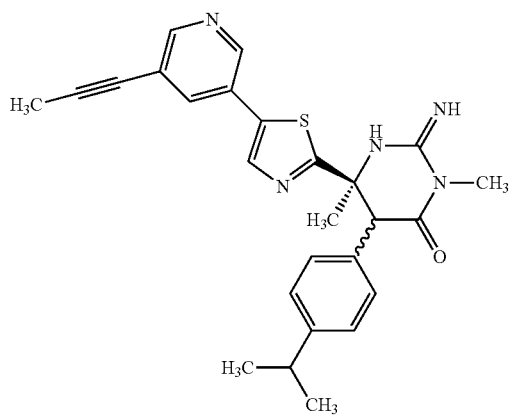
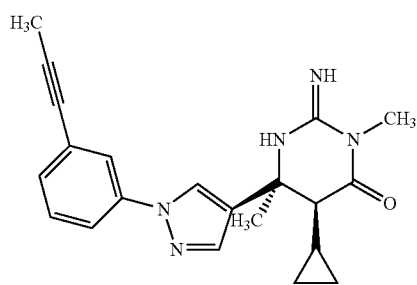
48
-continued
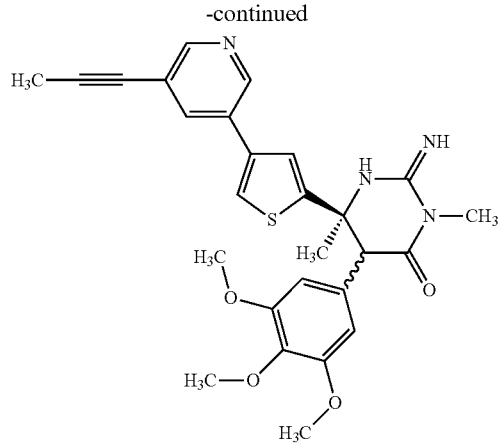
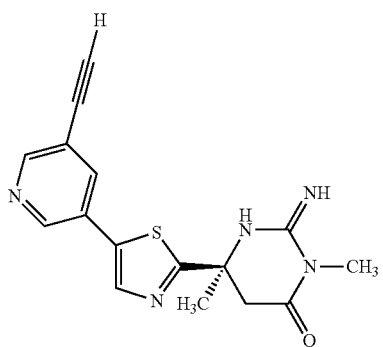
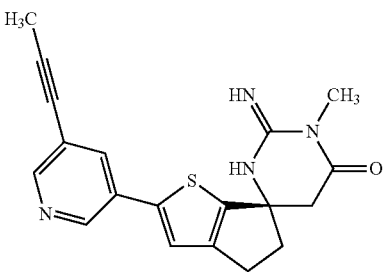
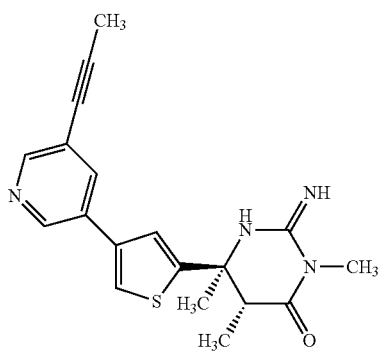

49
-continued
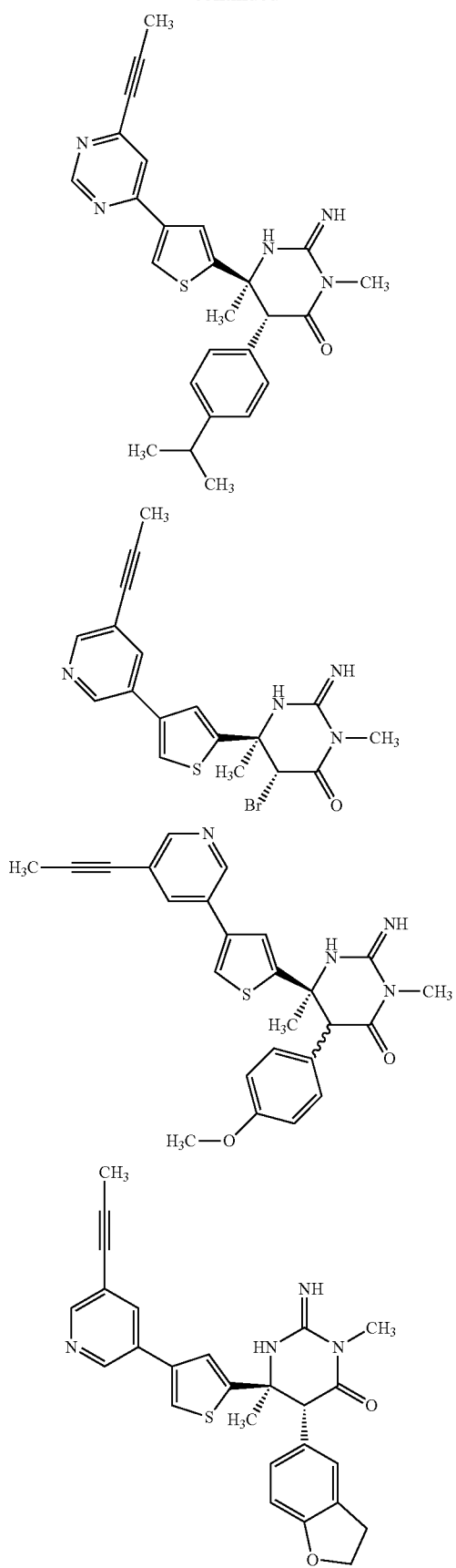
50
-continued
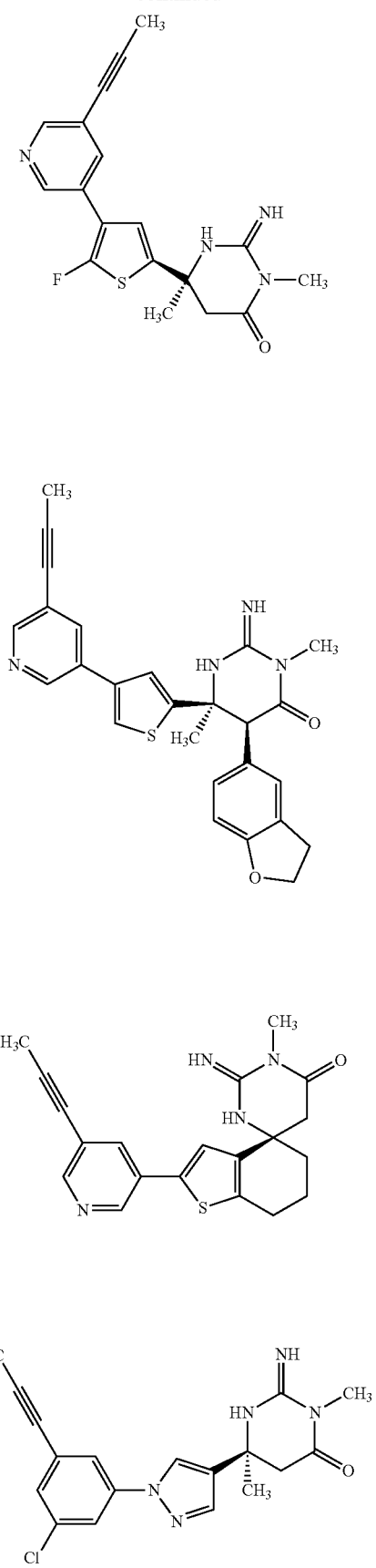

51
-continued
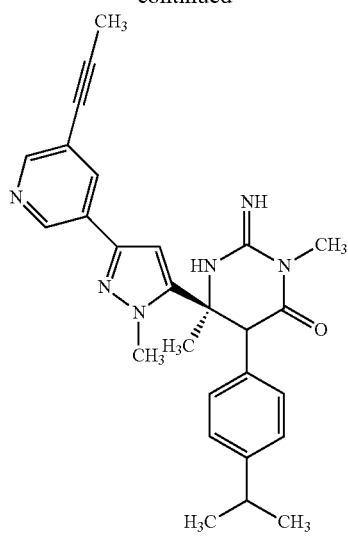
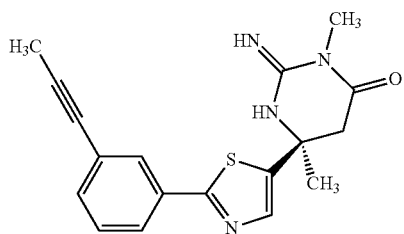
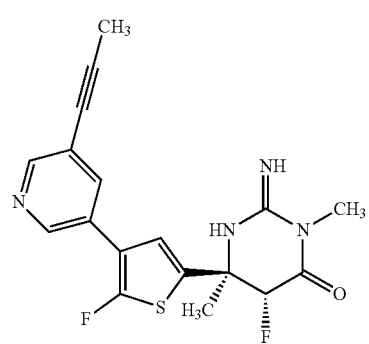
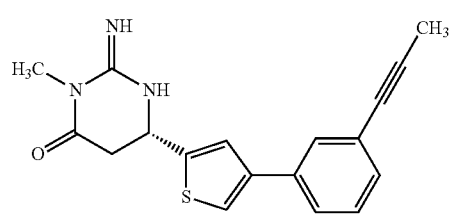
52
-continued
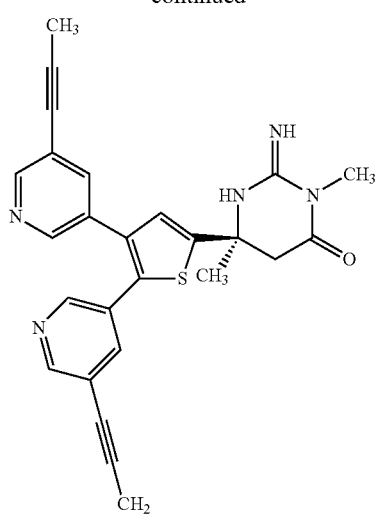
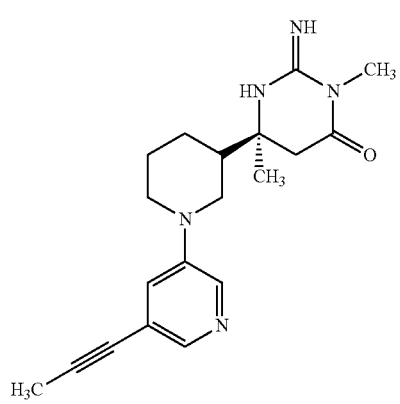
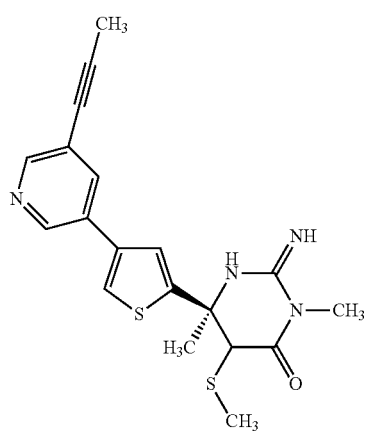

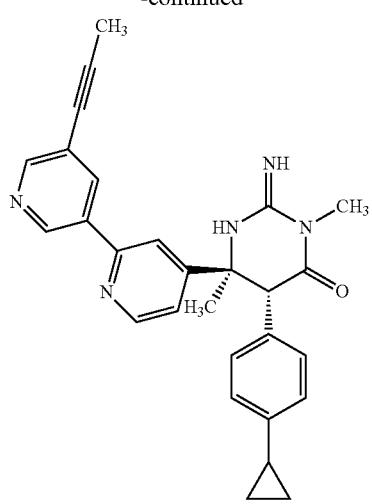
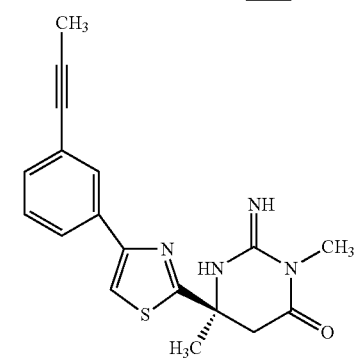
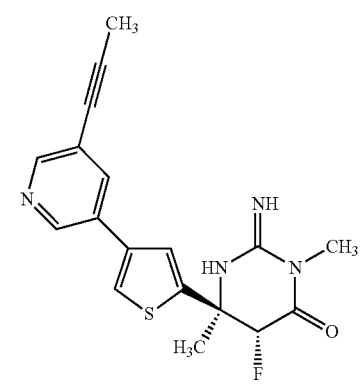
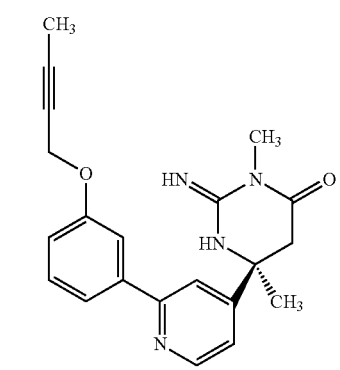
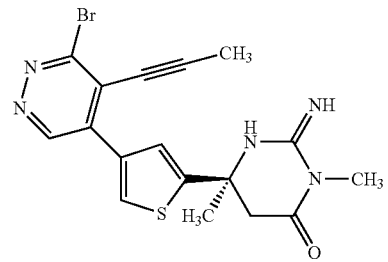
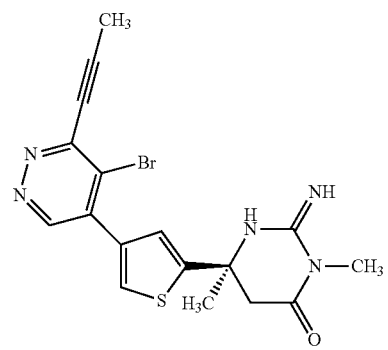
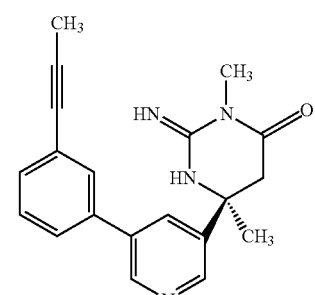
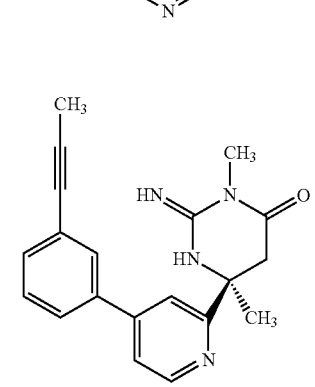
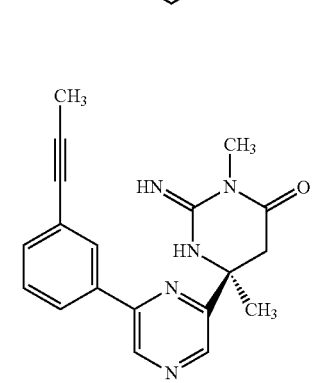

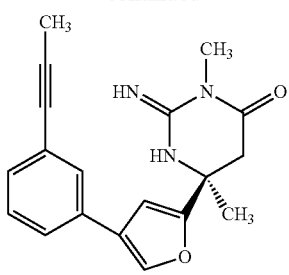

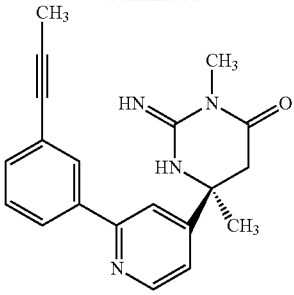

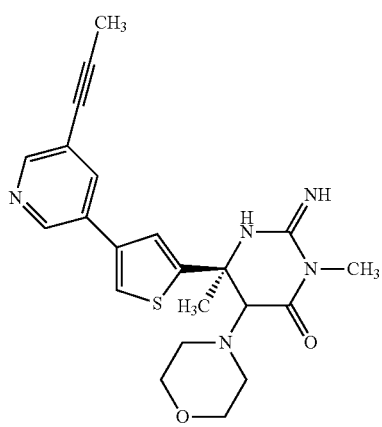

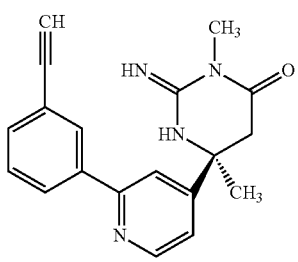

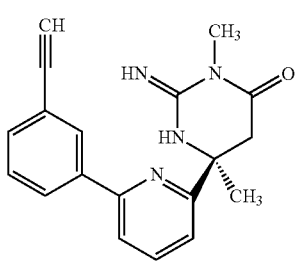

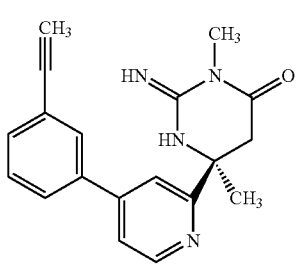

Human Cathepsin D FRET Assay

The substrate used below has been described (Y. Yasuda et al., J. Biochem., 125, 1137 (1999)). Substrate and enzyme are commercially available.

The assay can be run in a 30 μl final volume using a 384 well Nunc black plate. 8 concentrations of compound can be pre-incubated with enzyme for 30 mins at 37° C. followed by addition of substrate with continued incubation at 37° C. for 45 mins. The rate of increase in fluorescence is linear for over 1 h and is measured at the end of the incubation period using a Molecular Devices FLEX station plate reader. Kis are interpolated from the $IC_{50}$s using a Km value of 4 μM and the substrate concentration of 2.5 μM.

Reagents
Na-Acetate pH 5
1% Brij-35 from 10% stock (Calbiochem)
DMSO
Purified (>95%) human liver Cathepsin D (Athens Research & Technology Cat #16-12-030104)
Peptide substrate (Km=4 uM) Mca-Gly-Lys-Pro-Ile-Leu-Phe-Phe-Arg-Leu-Lys(Dnp)-D-Arg-$NH_2$ Bachem Cat #M-2455 Pepstatin is used as a control inhibitor (Ki~0.5 nM) and is available from Sigma.
Nunc 384 well black plates
Final Assay Buffer Conditions
100 mM Na Acetate pH 5.0
0.02% Brij-35
1% DMSO
Compound can be diluted to 3× final concentration in assay buffer containing 3% DMSO. 10 μl of compound will be added to 10 μl of 2.25 nM enzyme (3×) diluted in assay buffer without DMSO, mixed briefly, spun, and can be incubated at 37° C. for 30 mins. 3× substrate (7.5 μM) is prepared in 1× assay buffer without DMSO. 10 μl of substrate will be added to each well mixed and spun briefly to initiate the reaction. Assay plates can be incubated at 37 C for 45 mins and read on 384 compatible fluorescence plate reader using a 328 nm Ex and 393 nm Em.

BACE-1 Cloning, Protein Expression and Purification

A predicted soluble form of human BACE1 (sBACE1, corresponding to amino acids 1-454) can be generated from the full length BACE1 cDNA (full length human BACE1 cDNA in pCDNA4/mycHisA construct; University of Toronto) by PCR using the advantage-GC cDNA PCR kit (Clontech, Palo Alto, Calif.). A HindIII/PmeI fragment from pCDNA4-sBACE1 myc/His can be blunt ended using Klenow and subcloned into the Stu I site of pFASTBACI(A) (Invitrogen). A sBACE1 mycHis recombinant bacmid can be generated by transposition in DH10Bac cells (GIBCO/BRL). Subsequently, the sBACE1 mycHis bacmid construct can be transfected into sf9 cells using CellFectin (Invitrogen, San Diego, Calif.) in order to generate recombinant baculovirus. Sf9 cells are grown in SF 900-II medium (Invitrogen) supplemented with 3% heat inactivated FBS and 0.5× penicillin/streptomycin solution (Invitrogen). Five milliliters of high titer plaque purified sBACEmyc/His virus is used to infect 1 L of logarithmically growing sf9 cells for 72 hours. Intact cells are pelleted by centrifugation at 3000×g for 15 minutes. The supernatant, containing secreted sBACE1, is collected and diluted 50% v/v with 100 mM HEPES, pH 8.0. The diluted medium is loaded onto a Q-sepharose column. The Q-sepharose column is washed with Buffer A (20 mM HEPES, pH 8.0, 50 mM NaCl).

Proteins, can be eluted from the Q-sepharose column with Buffer B (20 mM HEPES, pH 8.0, 500 mM NaCl). The protein peaks from the Q-sepharose column are pooled and loaded onto a Ni-NTA agarose column. The Ni-NTA column can be then washed with Buffer C (20 mM HEPES, pH 8.0, 500 mM NaCl). Bound proteins are then eluted with Buffer D (Buffer C+250 mM imidazole). Peak protein fractions as determined by the Bradford Assay (Biorad, CA) are concentrated using a Centricon 30 concentrator (Millipore). sBACE1 purity is estimated to be ~90% as assessed by SDS-PAGE and Commassie Blue staining. N-terminal sequencing indicates that greater than 90% of the purified sBACE1 contained the prodomain; hence this protein is referred to as sproBACE1.

Peptide Hydrolysis Assay

The inhibitor, 25 nM EuK-biotin labeled APPsw substrate (EuK-KTEEISEVNLDAEFRHDKC-biotin (SEQ ID NO:1); CIS-Bio International, France), 5 µM unlabeled APPsw peptide (KTEEISEVNLDAEFRHDK (SEQ ID NO:2); American Peptide Company, Sunnyvale, Calif.), 7 nM sproBACE1, 20 mM PIPES pH 5.0, 0.1% Brij-35 (protein grade, Calbiochem, San Diego, Calif.), and 10% glycerol are preincubated for 30 min at 30° C. Reactions are initiated by addition of substrate in a 5 µl aliquot resulting in a total volume of 25 µl. After 3 hr at 30° C. reactions are terminated by addition of an equal volume of 2× stop buffer containing 50 mM Tris-HCl pH 8.0, 0.5 M KF, 0.001% Brij-35, 20 µg/ml SA-XL665 (cross-linked allophycocyanin protein coupled to streptavidin; CIS-Bio International, France) (0.5 µg/well). Plates are shaken briefly and spun at 1200×g for 10 seconds to pellet all liquid to the bottom of the plate before the incubation. HTRF measurements are made on a Packard Discovery® HTRF plate reader using 337 nm laser light to excite the sample followed by a 50 µs delay and simultaneous measurements of both 620 nm and 665 nm emissions for 400 µs.

$IC_{50}$ determinations for inhibitors, (I), are determined by measuring the percent change of the relative fluorescence at 665 nm divided by the relative fluorescence at 620 nm, (665/620 ratio), in the presence of varying concentrations of I and a fixed concentration of enzyme and substrate. Nonlinear regression analysis of this data can be performed using GraphPad Prism 3.0 software selecting four parameter logistic equation, that allows for a variable slope. Y=Bottom+(Top−Bottom)/(1+10^((LogEC50−X)*Hill Slope)); X is the logarithm of concentration of I, Y is the percent change in ratio and Y starts at bottom and goes to top with a sigmoid shape.

Human Mature Renin Enzyme Assay

Human Renin can be cloned from a human kidney cDNA library and C-terminally epitope-tagged with the V5-6His sequence into pCDNA3.1. pCDNA3.1-Renin-V5-6His is stably expressed in HEK293 cells and purified to >80% using standard Ni-Affinity chromatography. The prodomain of the recombinant human renin-V5-6His can be removed by limited proteolysis using immobilized TPCK-trypsin to give mature-human renin. Renin enzymatic activity can be monitored using a commercially available fluorescence resonance energy transfer (FRET) peptide substrate, RS-1 (Molecular Probes, Eugene, Oreg.) in 50 mM Tris-HCl pH 8.0, 100 mM NaCl, 0.1% Brij-35 and 5% DMSO buffer for 40 mins at 30° Celsius in the presence or absence of different concentrations of test compounds. Mature human Renin is present at approximately 200 nM. Inhibitory activity is defined as the percent decrease in renin induced fluorescence at the end of the 40 min incubation compared to vehicle controls and samples lacking enzyme.

In the aspect of the invention relating to a combination of at least one compound of formula I with at least one cholinesterase inhibitor, acetyl- and/or butyrylcholinesterase inhibitors can be used. Examples of cholinesterase inhibitors are tacrine, donepezil, rivastigmine, galantamine, pyridostigmine and neostigmine, with tacrine, donepezil, rivastigmine and galantamine being preferred. Preferably, these combinations are directed to the treatment of Alzheimer's Disease.

In one aspect of the invention, a combination of at least one compound of formula I with at least one muscarinic $m_1$ agonist or $m_2$ antagonist can be used. Examples of $m_1$ agonists are known in the art. Examples of $m_2$ antagonists are also known in the art; in particular, $m_2$ antagonists are disclosed in U.S. Pat. Nos. 5,883,096; 6,037,352; 5,889,006; 6,043,255; 5,952,349; 5,935,958; 6,066,636; 5,977,138; 6,294,554; 6,043,255; and 6,458,812; and in WO 03/031412, all of which are incorporated herein by reference.

In other aspects of the invention relating to a combination of at least one compound of formula I and at least one other agent, for example a beta secretase inhibitor; a gamma secretase inhibitor; an HMG-CoA reductase inhibitor such as atorvastatin, lovastatin, simvastatin, pravastatin, fluvastatin and rosuvastatin; non-steroidal anti-inflammatory agents such as, but not necessarily limited to ibuprofen, relafen or naproxen; N-methyl-D-aspartate receptor antagonists such as memantine; anti-amyloid antibodies including humanized monoclonal antibodies; vitamin E; nicotinic acetylcholine receptor agonists; CB1 receptor inverse agonists or CB1 receptor antagonists; antibiotics such as doxycycline; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity. Preferably, these combinations are directed to the treatment of Alzheimer's Disease.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

When a compound of formula I is used in combination with a cholinesterase inhibitor to treat cognitive disorders, these two active components may be co-administered simultaneously or sequentially, or a single pharmaceutical composition comprising a compound of formula I and a cholinesterase inhibitor in a pharmaceutically acceptable carrier can be administered. The components of the combination can be administered individually or together in any conventional oral or parenteral dosage form such as capsule, tablet, powder, cachet, suspension, solution, suppository, nasal spray, etc. The dosage of the cholinesterase inhibitor can be determined from published material, and may range from 0.001 to 100 mg/kg body weight.

When separate pharmaceutical compositions of a compound of formula I and a cholinesterase inhibitor are to be administered, they can be provided in a kit comprising in a single package, one container comprising a compound of formula I in a pharmaceutically acceptable carrier, and a separate container comprising a cholinesterase inhibitor in a pharmaceutically acceptable carrier, with the compound of formula I and the cholinesterase inhibitor being present in amounts such that the combination is therapeutically effective. A kit is advantageous for administering a combination when, for example, the components must be administered at different time intervals or when they are in different dosage forms.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

```
                         SEQUENCE LISTING

<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: peptide substrate
<220> FEATURE:
<221> NAME/KEY: MISC_FEATURE
<222> LOCATION: (1)..(1)
<223> OTHER INFORMATION: N-terminal modification with Maurocalcine
<220> FEATURE:
<221> NAME/KEY: MISC_FEATURE
<222> LOCATION: (10)..(10)
<223> OTHER INFORMATION: 2,4-dinitrophenyl modified Lysine 10

<400> SEQUENCE: 1

Gly Lys Pro Ile Leu Phe Phe Arg Leu Lys Arg
1               5                   10
```

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

We claim:

1. A compound having the structural formula I

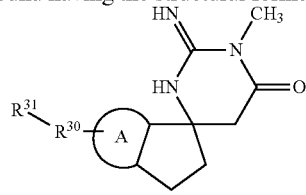

or a stereoisomer, tautomer, or pharmaceutically acceptable salt thereof, wherein
ring A is phenyl or thienyl;
$R^{30}$ is selected from the group consisting of cyclopentyl, cyclohexyl, phenyl, and heteroaryl;
$R^{31}$ is

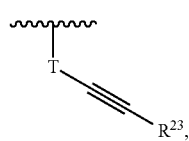

wherein T is a bond, —O—((C($R^{23}$)($R^{23}$))—, —S—((C($R^{23}$)($R^{23}$)—, —NH—((C($R^{23}$)( $R^{23}$))— or —((C($R^{23}$)($R^{23}$))$_{1-3}$—; and
$R^{23}$ is H.

2. A compound of claim 1 wherein T is a bond or —CH$_2$—.
3. A compound of claim 1 wherein $R^{31}$ is

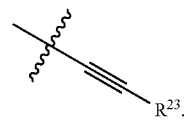

4. A compound having a structure:

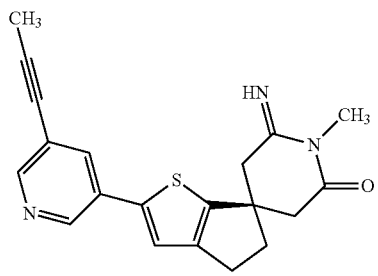

or a pharmaceutically acceptable salt thereof.

5. A pharmaceutical composition comprising an effective amount of a compound of claim 1, or a pharmaceutically acceptable salt thereof, and a pharmaceutically effective carrier.

6. A pharmaceutical composition comprising an effective amount of a compound of claim 4, or a pharmaceutically acceptable salt thereof, and a pharmaceutically effective carrier.

* * * * *